United States Patent
Exner et al.

(10) Patent No.: US 10,973,935 B2
(45) Date of Patent: *Apr. 13, 2021

(54) STABILIZED NANOBUBBLES FOR DIAGNOSTIC AND THERAPEUTIC APPLICATIONS

(71) Applicant: CASE WESTERN RESERVE UNIVERSITY, Cleveland, OH (US)

(72) Inventors: Agata Exner, Westlake, OH (US); Tianyi Krupka, Westlake, OH (US); Luis Solorio, University Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/519,834

(22) Filed: Jul. 23, 2019

(65) Prior Publication Data

US 2020/0061220 A1    Feb. 27, 2020

Related U.S. Application Data

(63) Continuation of application No. 13/825,941, filed as application No. PCT/US2011/053272 on Sep. 26, 2011, now Pat. No. 10,357,575.

(60) Provisional application No. 61/386,193, filed on Sep. 24, 2010.

(51) Int. Cl.
*A61K 49/22* (2006.01)
*A61K 9/127* (2006.01)

(52) U.S. Cl.
CPC .......... *A61K 49/223* (2013.01); *A61K 9/1271* (2013.01)

(58) Field of Classification Search
None
See application file for complete search history.

(56) References Cited

U.S. PATENT DOCUMENTS

| 6,572,840 | B1 | 6/2003 | Toler |
| 7,452,551 | B1 | 11/2008 | Unger et al. |
| 2003/0003055 | A1 | 1/2003 | Unger et al. |
| 2008/0206187 | A1 | 8/2008 | Exner et al. |
| 2008/0279929 | A1 | 11/2008 | Devane et al. |
| 2008/0311045 | A1 | 12/2008 | Hardy |
| 2009/0117177 | A1* | 5/2009 | Rapoport ............. A61K 49/223 424/450 |

OTHER PUBLICATIONS

Feshitan et al., "Microbubble size isolation by differential centrifugation", 2009 J. Colloid Interface Sci. 329: 316-324. Published online Oct. 1, 2008.
Liu et al., "The preparation and characterization of gas bubble containing liposomes", 2005 IEEE Engineering in Medicine and Biology 27th Annual Conference, Shanghai; p. 3998-4001.
Unger et al., "Therapeutic applications of lipid-coated microbubbles", 2004 Adv. Drug Deliv. Rev. 56: 1291-1314.
Unger et al., "Acoustically active liposheres containing paclitaxel: a new therapeutic ultrasound contrast agent", 1998 Invest. Radiol. 33: 886-892. 9 p. copy provided.
Oh et al., "Micellar formulations for drug delivery based on mixtures of hydrophobic and hydrophilic Pluronic block copolymers", 2004 J. Control. Release 94: 411-422.
Krupka et al., "Formulation and characterization of echogenic lipid-Pluronic nanobubbles", on line Dec. 3, 2009, 2010 Mol. Pharm. 7: 49-59.
Yin, et al., "Nanobubbles for enhanced ultrasound imaging of tumors", International journal of Nanomedicine 2012:7 895-904.

* cited by examiner

*Primary Examiner* — Jennifer Lamberski
(74) *Attorney, Agent, or Firm* — Tarolli, Sundheim, Covell & Tummino LLP

(57) ABSTRACT

A stabilized nanobubble can include a membrane that defines at least one internal void, which includes at least one gas. The membrane can include at least one lipid and at least one nonionic triblock copolymer that is effective to control the size of the nanobubble without compromising in vitro and in vivo echogenicity of the nanobubble.

23 Claims, 17 Drawing Sheets

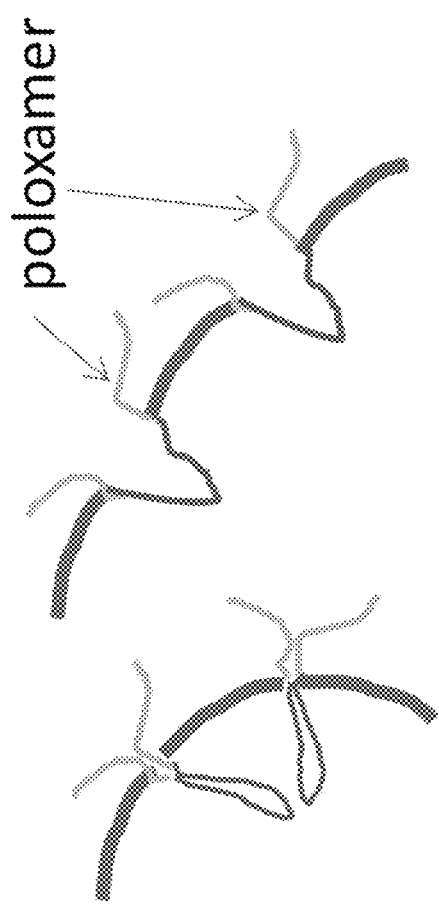
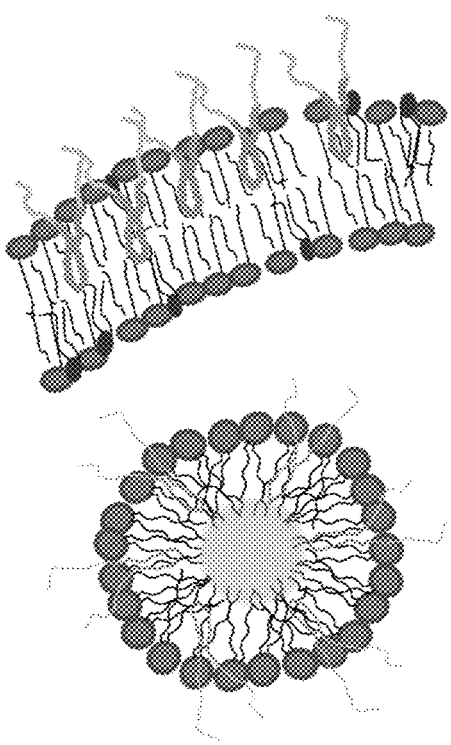
Fig. 3

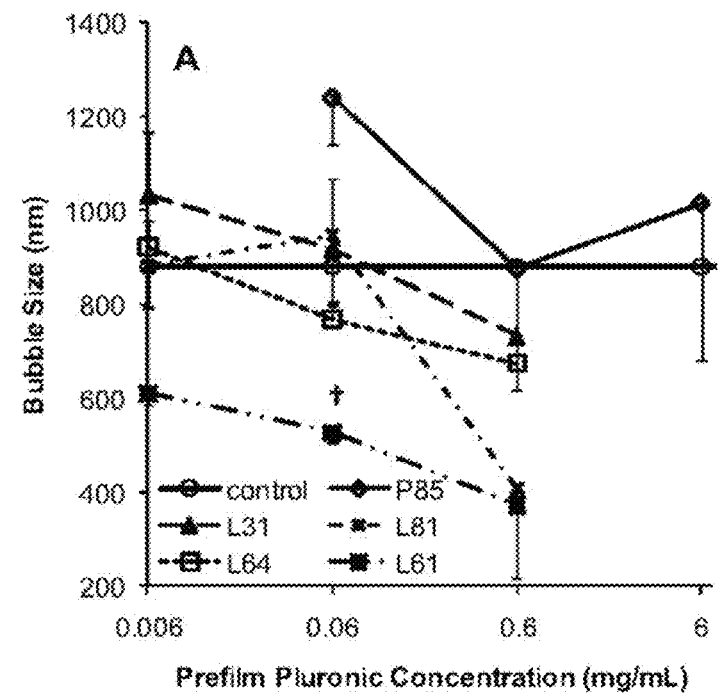
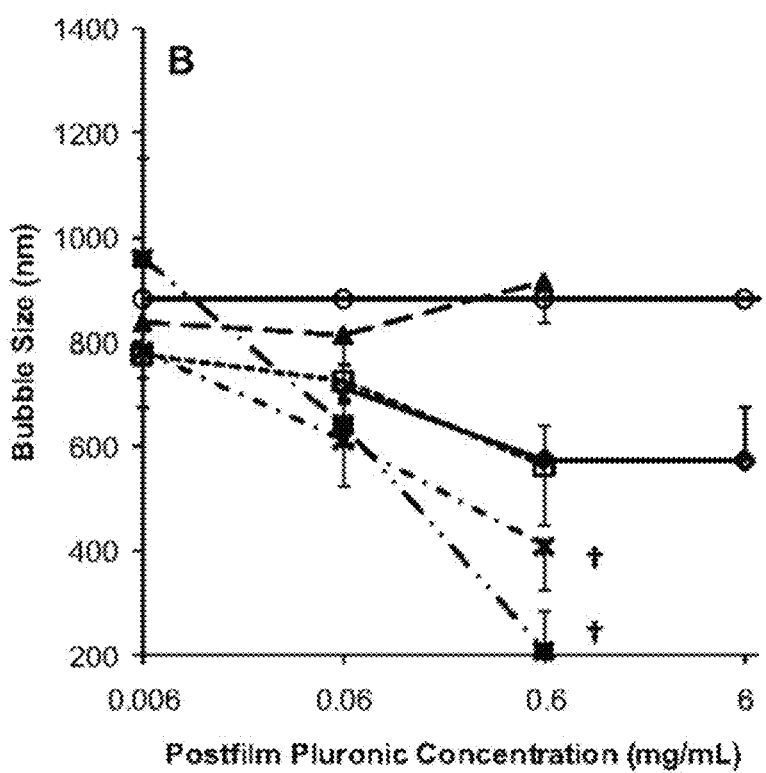
Figs. 6A-B

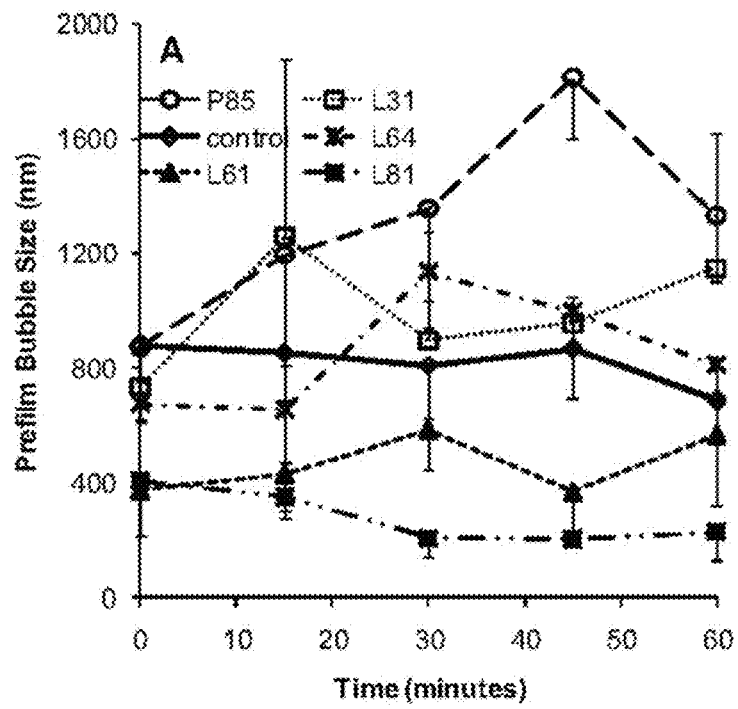
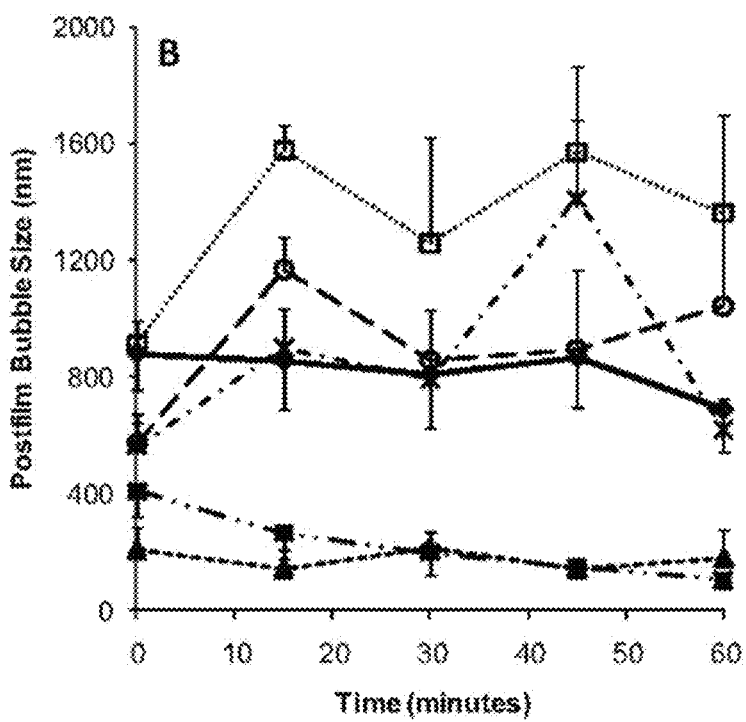
Figs. 7A-B

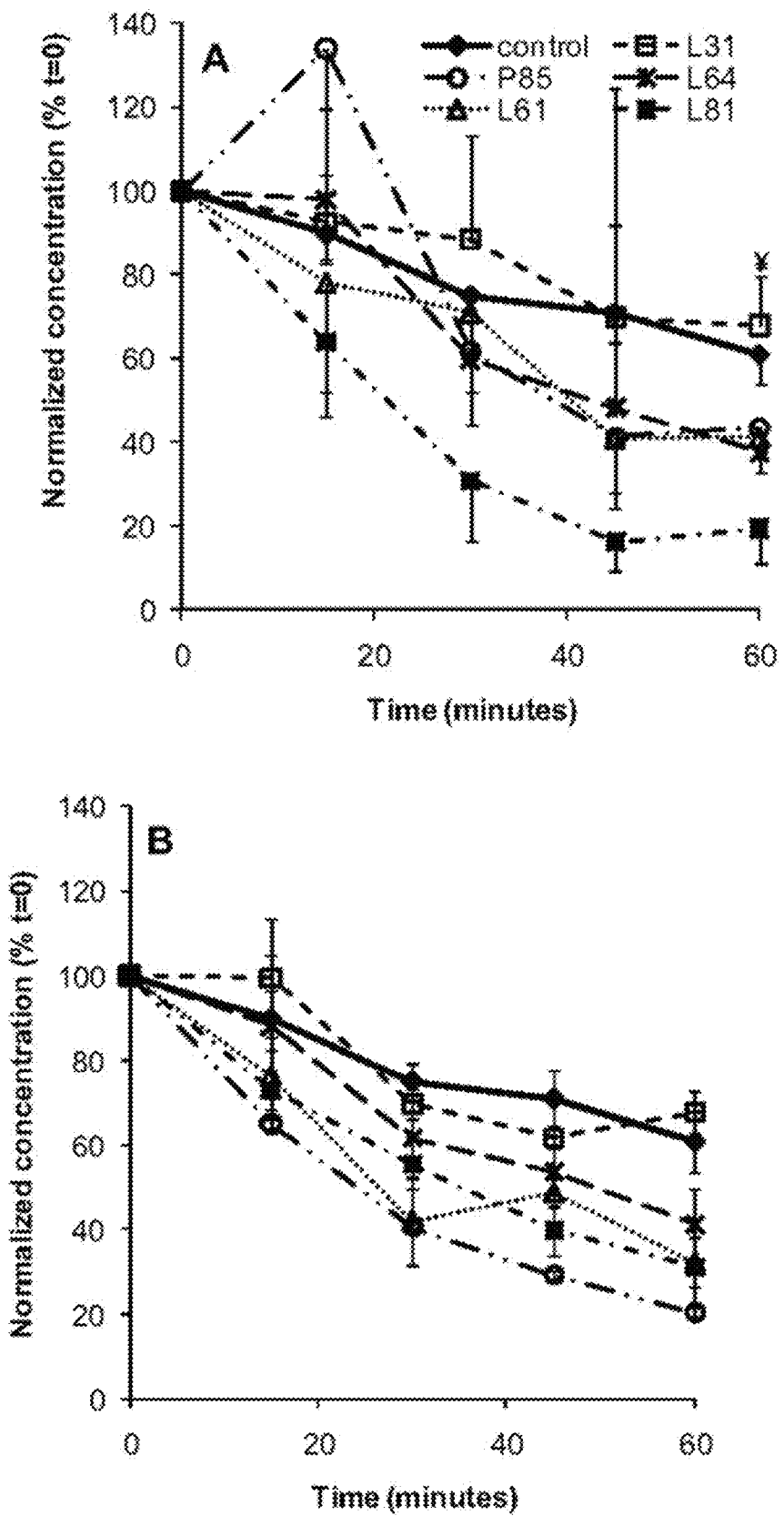
Figs. 8A-B

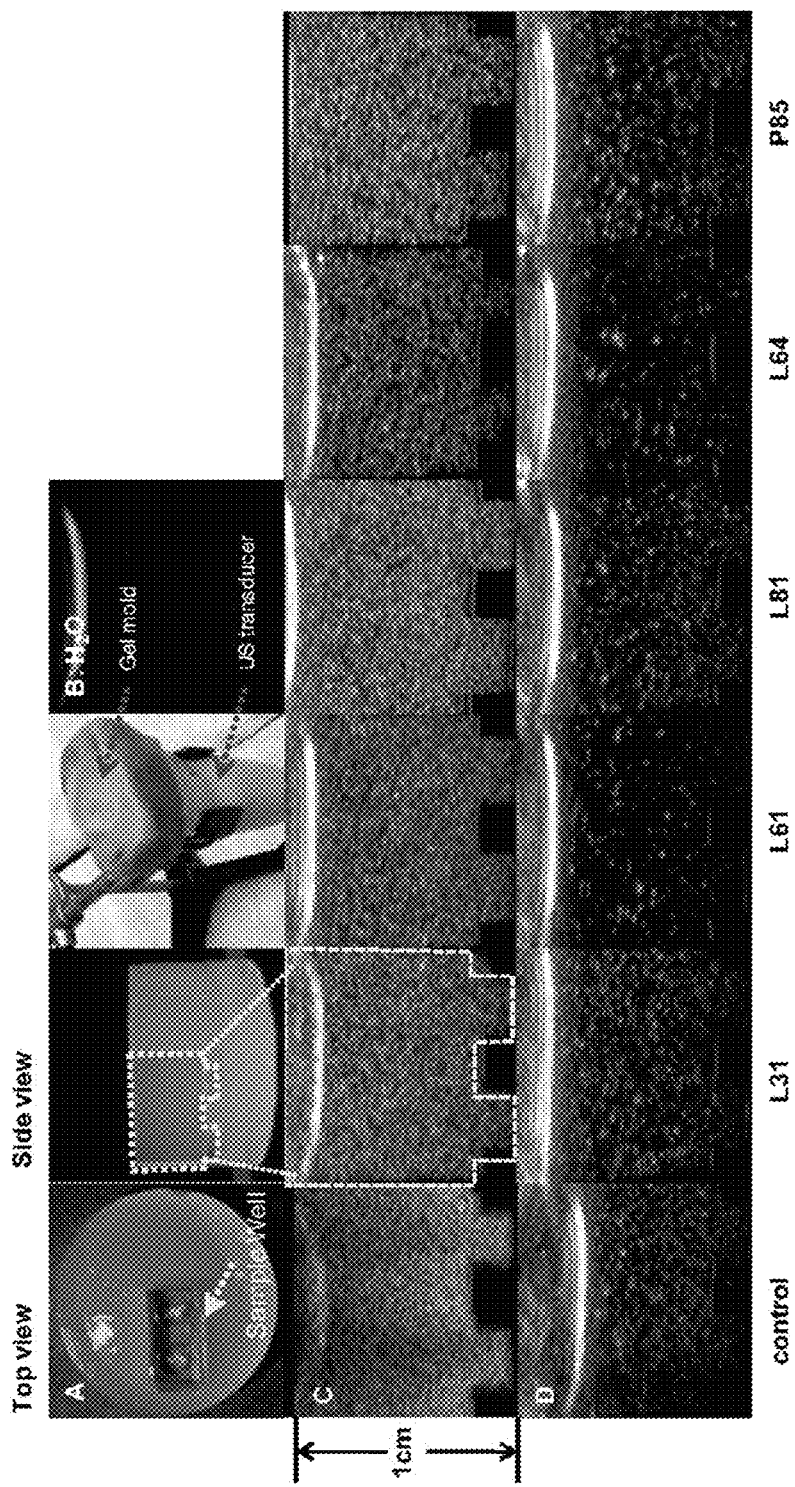
Figs. 9A-D

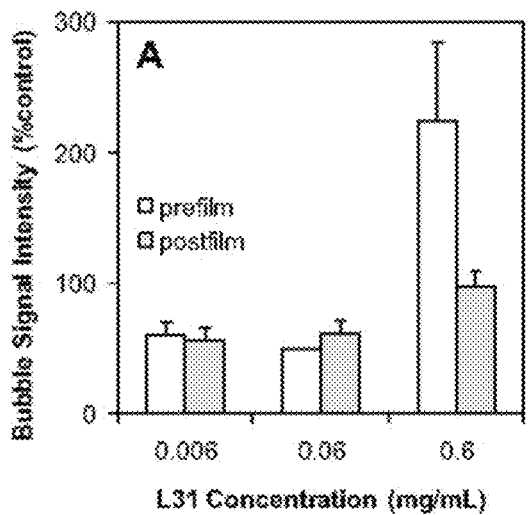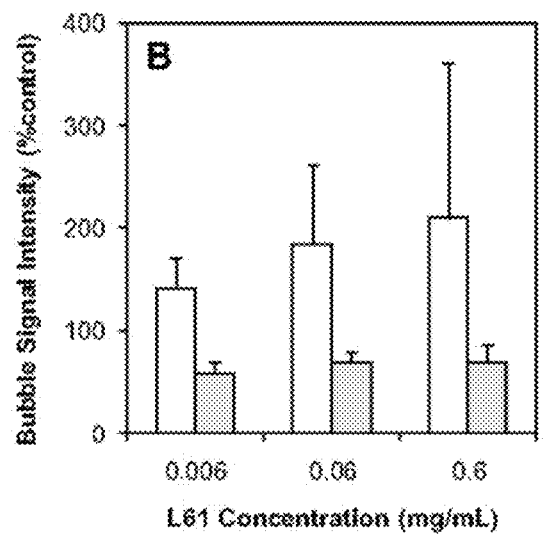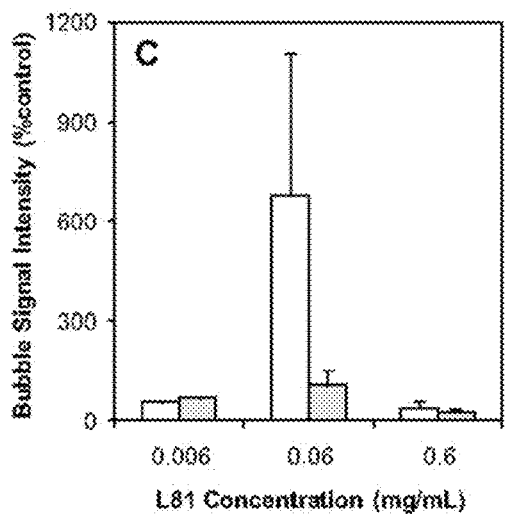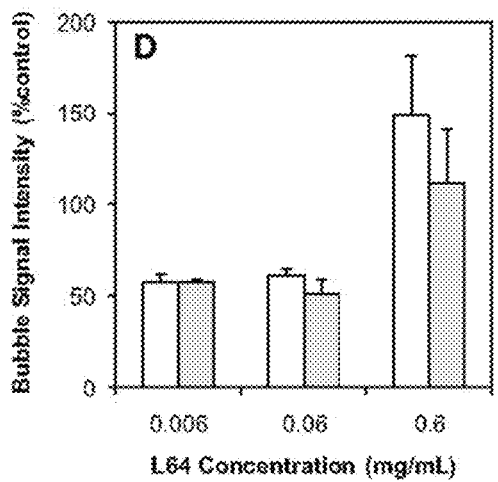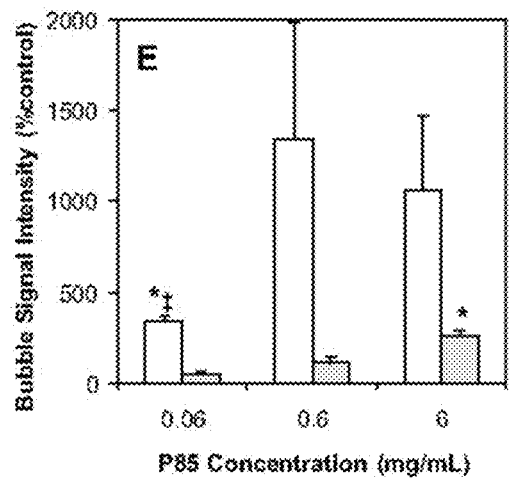
Figs. 10A-E

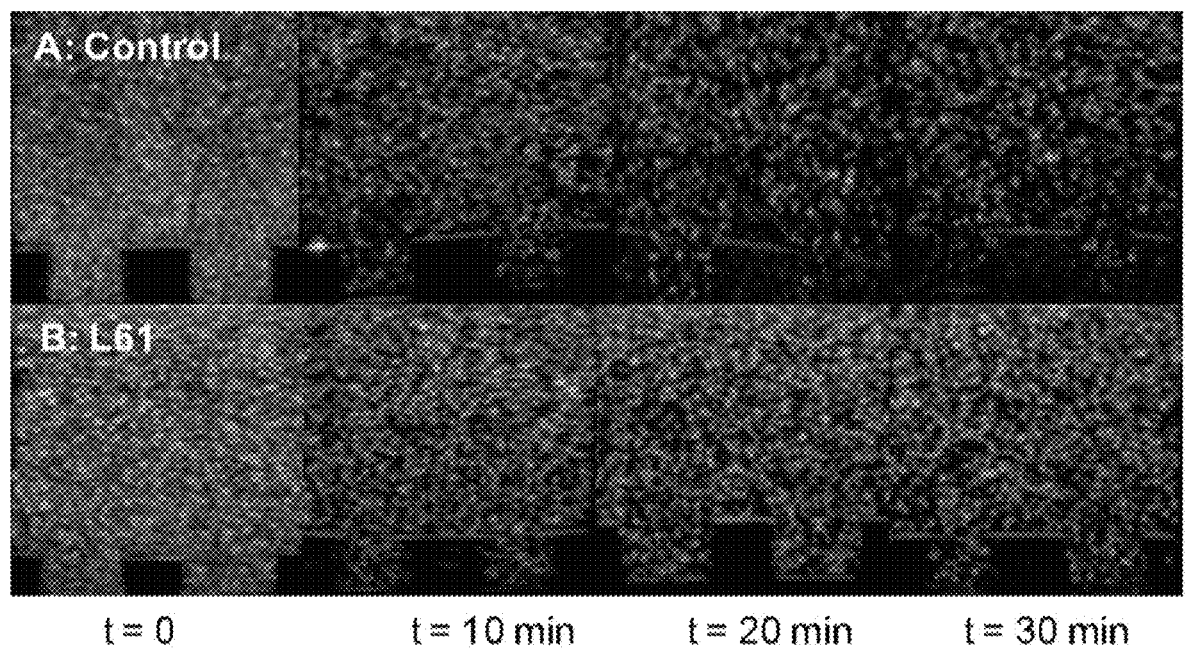
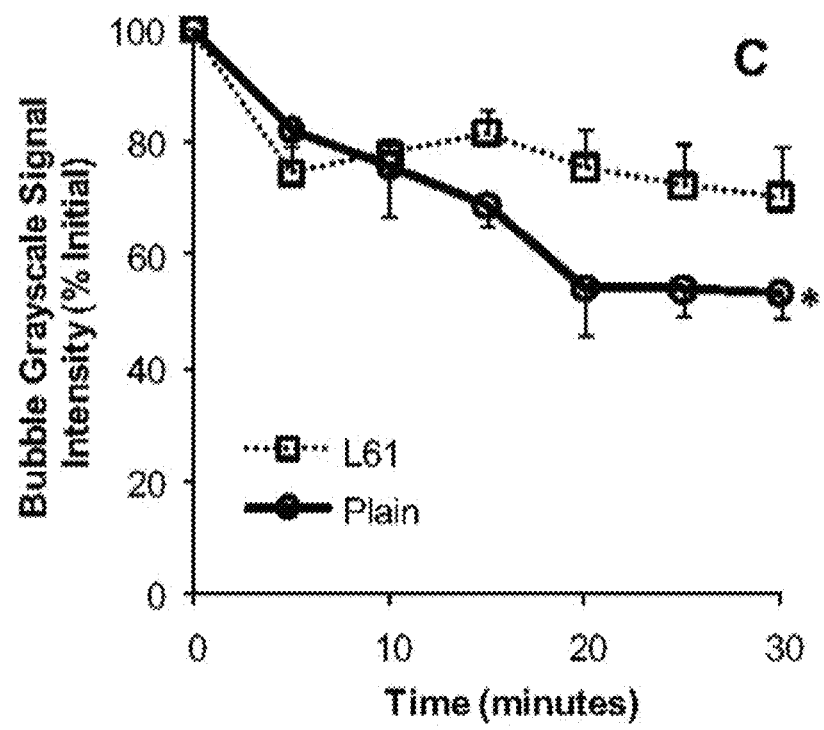
Figs. 11A-C

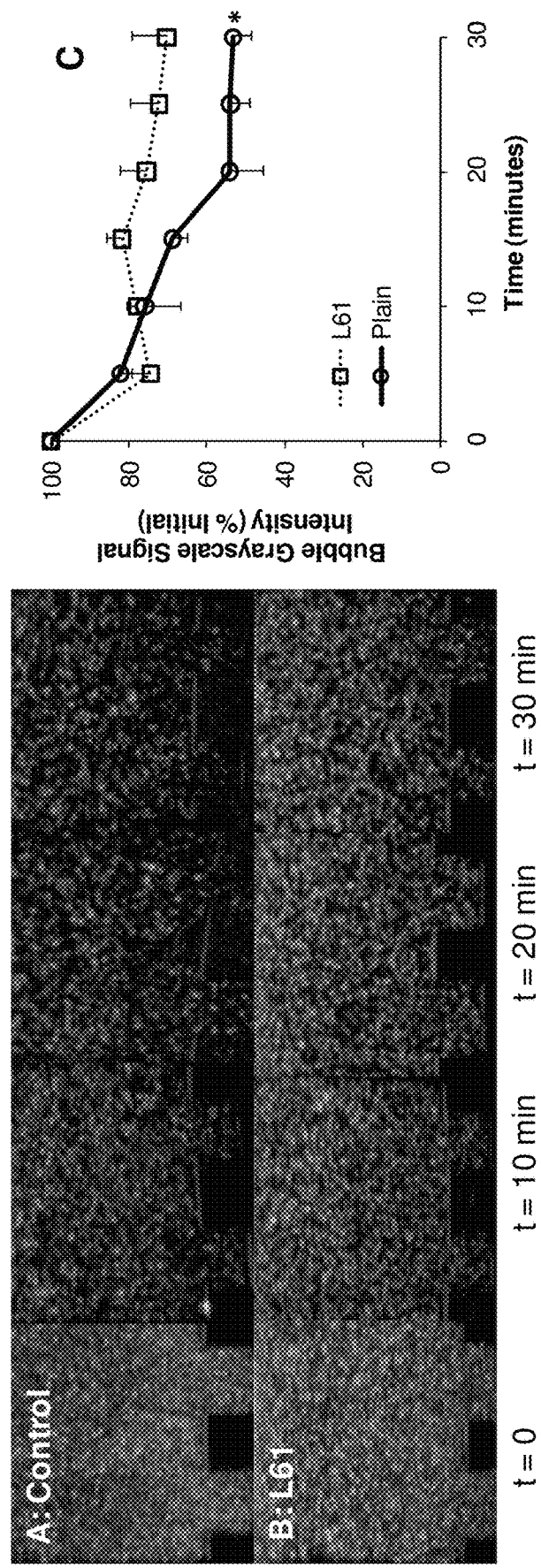
Figs. 12A-C

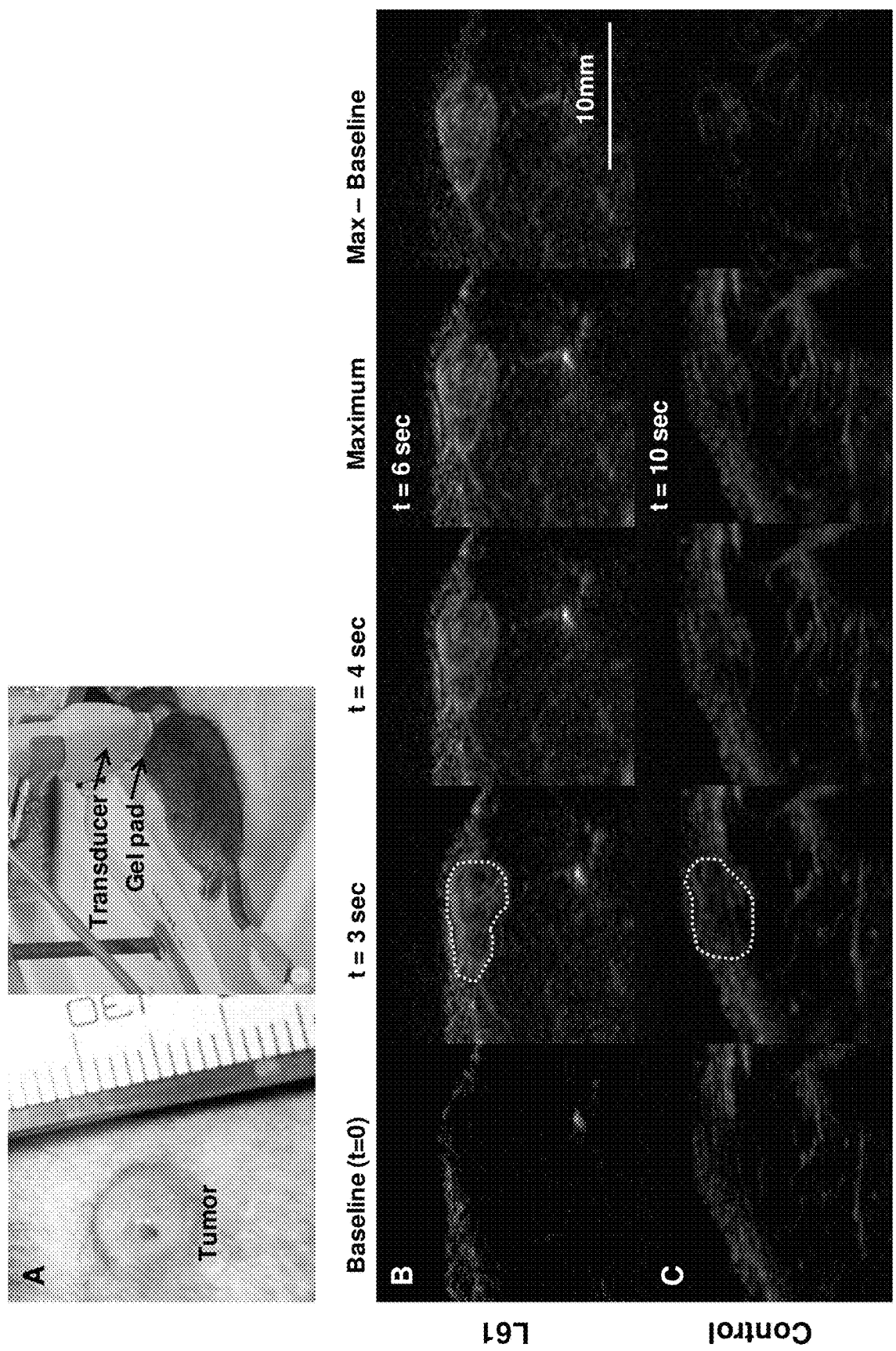
Figs. 13A-C

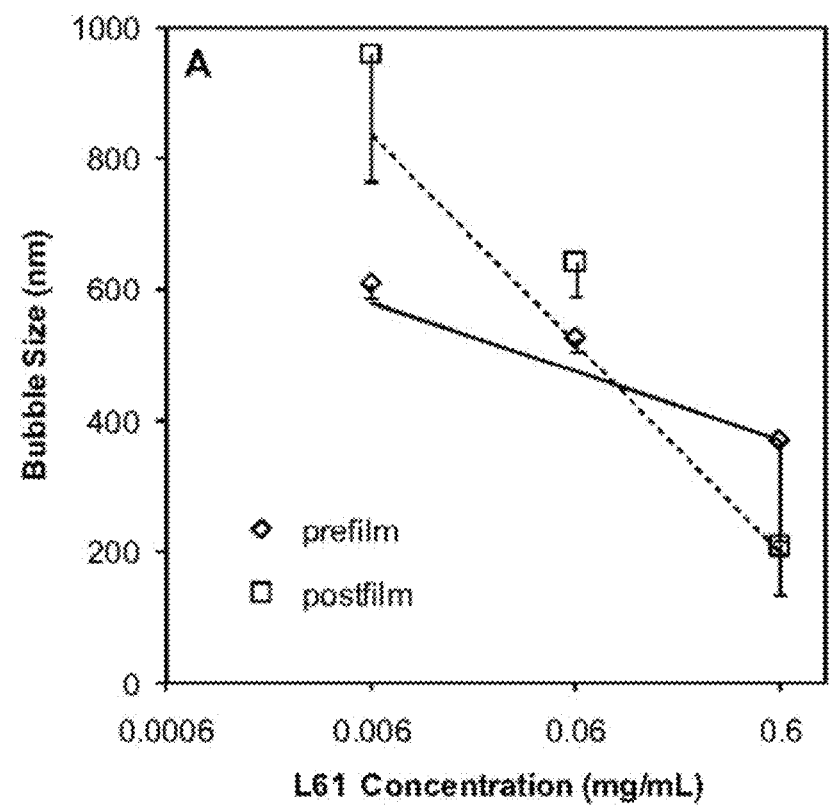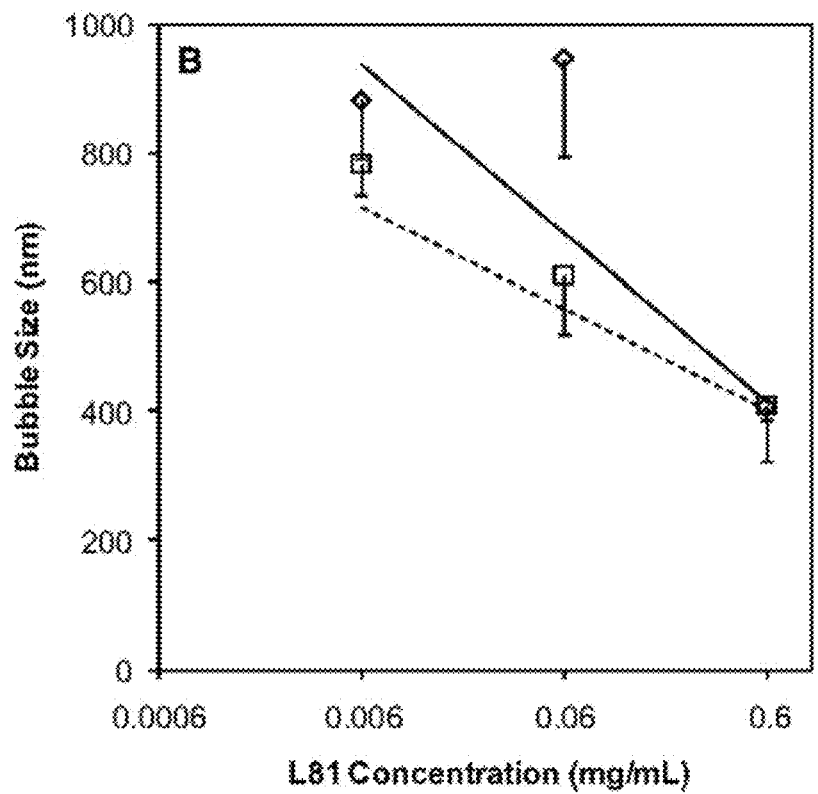
Figs. 15A-B

STABILIZED NANOBUBBLES FOR DIAGNOSTIC AND THERAPEUTIC APPLICATIONS

RELATED APPLICATION

This application claims priority from U.S. Provisional Application No. 61/386,193, filed Sep. 24, 2010, the subject matter of which is incorporated herein by reference in its entirety.

GOVERNMENT FUNDING

This invention was made with government support under Grant No. CA118399 and CA136857 awarded by The National Institute of Health and The National Cancer Institute. The United States government may have certain rights to the invention.

TECHNICAL FIELD

This application relates to diagnostic and therapeutic compositions, and more particularly to stabilized nanobubbles for diagnostic, therapeutic, and theranostic applications.

BACKGROUND OF THE INVENTION

Ultrasound contrast agents (UCA) are small gas-filled bubbles with a stabilizing shell made from a variety of materials, such as polymer, protein or lipid. Other than the traditional applications of these agents in diagnostic ultrasound imaging, UCA have found relevance in therapeutic applications including targeted gene and drug delivery. These adaptable particles are currently being explored as protective therapeutic carriers and as cavitation nuclei to enhance delivery of their payload by sonoporation. Together these functions improve payload circulation half-life and release profiles as well as tissue selectivity and cell uptake. Regardless of the mode of action, it is advantageous, particularly in cancer therapy, for the bubbles to extravasate from the vasculature and arrive at the cellular target site for the desired effect.

Commercial UCA available today are typically designed to serve only as blood pool agents with diameters of 1-8 μm. Although previous methodologies have been developed to reduce bubble size, most of these strategies involve manipulations of microbubbles post formation, such as gradient separation by gravitational forces or by physical filtration or floatation. While effective for selecting nanosized bubbles, these methods introduce potential for sample contamination, reduce bubble yield and stability, and waste stock materials in addition to being labor intensive. Additionally, the applicability of microbubbles as carriers (e.g., in cancer therapy) has been limited by a large size, which typically confines them to the vasculature.

SUMMARY OF THE INVENTION

This application relates to stabilized nanobubbles for diagnostic and therapeutic applications. The stabilized nanobubbles can be used as multifunctional and/or theranostic platforms for molecular imaging, drug therapy, gene therapy, chemotherapy, and anti-microbial applications. The stabilized nanobubble can include a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble.

In an aspect of the application, the nonionic triblock copolymer can include at least one poloxamer. The poloxamer can have a molecular, for example, of about 1100 Daltons to about 3000 Daltons. The concentration of nonionic triblock copolymer in the lipid nanobubble can be about 0.06 mg/ml to about 1 mg/ml. The gas can have a low solubility in water and include, for example, a perfluorocarbon, such as perfluoropropane, carbon dioxide, and air.

In another aspect, the nanobubble can have a size that facilitates extravasation of the nanobubble in cancer therapy or diagnosis. For example, the nanobubble can have a diameter or size of about 50 nm to about 800 nm (or about 50 nm to about 400 nm).

In a further aspect, the nanobubble can include at least one targeting moiety that is linked to the membrane. The targeting moiety can be selected from the group consisting of polypeptides, polynucleotides, small molecules, elemental compounds, antibodies, and antibody fragments.

In a still further aspect, the nanobubble can include at least one therapeutic agent that is contained within the membrane or conjugated to the membrane. The therapeutic agent can include at least one chemotherapeutic agent, anti-proliferative agent, biocidal agent, biostatic agent, or anti-microbial agent.

Another aspect of the application relates to a method for forming a composition comprising at least one stabilized nanobubble. The method can include the steps of: (a) dissolving at least one lipid in a solvent; (b) evaporating the solvent to produce a film; (c) hydrating the film; and (d) removing air, injecting gas and shaking a solution of the hydrated film to form the at least one nanobubble. At least one nonionic triblock copolymer can be added at either step (a) or step (c) to control the size of the at least one nanobubble.

A further aspect of the application relates to a method for imaging a region of interest (ROI) in a subject. The method can include administering to the subject a composition comprising a plurality of stabilized nanobubbles. Each of the nanobubbles can have a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble. After administering the composition to the subject, at least one image of the ROI can be generated.

A further aspect of the application relates to a method for treating a neoplastic disorder in a subject. The method can include administering to neoplastic cells of the subject a composition comprising a plurality of stabilized nanobubbles. Each of the nanobubbles can have a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble.

The method can further include applying a cellular stress to the neoplastic cells of the subject. The cellular stress can be applied at an amount or level effective to induce heat shock protein (HSP) expression in the neoplastic cells. The plurality of nanobubbles can be administered to the neoplastic cells at an amount effective to substantially inhibit HSP expression and/or function in the neoplastic cells.

Another aspect of the application relates to a method of sensitizing a microorganism to an antimicrobial agent. The method includes administering to the microorganism a composition comprising a plurality of stabilized nanobubbles. Each of the nanobubbles can have a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble. The plurality of nanobubbles can be administered at an amount effective to substantially inhibit HSP expression in the microorganism.

Yet another aspect of the application relates to an antimicrobial composition that includes at least one biocidal agent or biostatic agent that can induce or promote HSP expression in the microorganism and a plurality of stabilized nanobubbles. Each of the nanobubbles can have a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble. The nanobubbles can be effective to substantially inhibit HSP expression and/or function induced or promoted by the biocidal agent or biostatic agent in the microorganism.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 3 is a schematic illustration of a proposed mechanism of highly echogenic nanobubbles in accordance with an aspect of the application.

FIGS. 6A-B are plots illustrating bubble size in the presence of 0.006, 0.06, 0.6 and 6 mg/mL of Pluronic that was incorporated into the bubble formulation before (A: preflim) or after (B: postfilm) lipid film hydration (mean±SEM; n=3). † indicate statistically significant difference compared to control (P: 0.001-0.01).

FIGS. 7A-B are plots illustrating bubble size distribution change as a function of time. Data presented for control bubbles and bubbles with 0.6 mg/mL of Pluronic (mean±SEM; n=3). (A) prefilm; (B) postfilm.

FIGS. 8A-B are plots illustrating bubble concentration change as a function of time (A: preflim; B: postfilm; P:0.0001-0.023). Data presented as mean±SEM (n=3). ¥ indicates the only condition that showed no significant difference at t=60 min vs. t=0 (P=0.1).

FIGS. 9A-D are pluronic bubble grayscale ultrasound images in vitro in custom-made agarose gel mold and experimental setup (A); dashed line indicates sample well; (B) US image of $H_2O$; (C) bubbles with 0.6 mg/mL of L31, L61, L81, L64 and P85 at same dilutions; (D) control, bubbles with 0.6 mg/mL of L31, L61, L81, L64 and P85 at equivalent bubble concentrations.

FIGS. 10A-E are charts showing a quantitative analysis of grayscale ultrasound signal intensity of bubbles in the presence of 0.006, 0.06, 0.6 and 6 mg/mL of Pluronic that were incorporated in the formulation before or after lipid film hydration (Mean±SEM; n=3). * indicates statistically significant higher compared to control (P: 0.0006-0.008); and ‡ indicates statistically significant differences compared to postfilm bubble signals under the same conditions (P=0.003). (A) L31; (B) L61; (C) L81; (D) L64; E: P85.

FIGS. 11(A-C) illustrate (A) representative ultrasound images of control microbubbles, (B) L61 nanobubbles over 30 minutes; and (C) a plot of quantitative grayscale ultrasound signal intensity (% of initial value). The initial values of the bubble grayscale signal intensities were 79.1±3.0 for control and 74.8±16.3 for L61 bubbles (Mean±SEM; n=3). * indicates statistically significant difference compared to initial value (P=0.0006).

FIGS. 12(A-C) illustrate (A) perfusion imaging of representative subcutaneous tumor; (B) an example of the mosaic image used to determine quality of fit for the registration; (C) ultrasound images at t=0, 10 sec, 5 min and 20 min after injection of control or L61 bubbles. Dotted lines outline the tumors; and (D) a plot of quantitative summary of tumor enhancement after contrast administration presented as fold of increase in signal intensity relative to baseline images.

FIGS. 13(A-C) illustrate tumor microflow imaging of (A) representative subcutaneous tumor and experimental setup; (B) microflow images of tumor after L61 nanobubble administration; (C) the same tumor after control microbubble administration. Dashed lines indicate the tumor location. Baseline image is the first video frame immediately after flash.

FIGS. 15(A-B) are plots illustrating bubble size dependence on Pluronic concentration. (A) L61; (B) L81.

DETAILED DESCRIPTION

Figure 1:
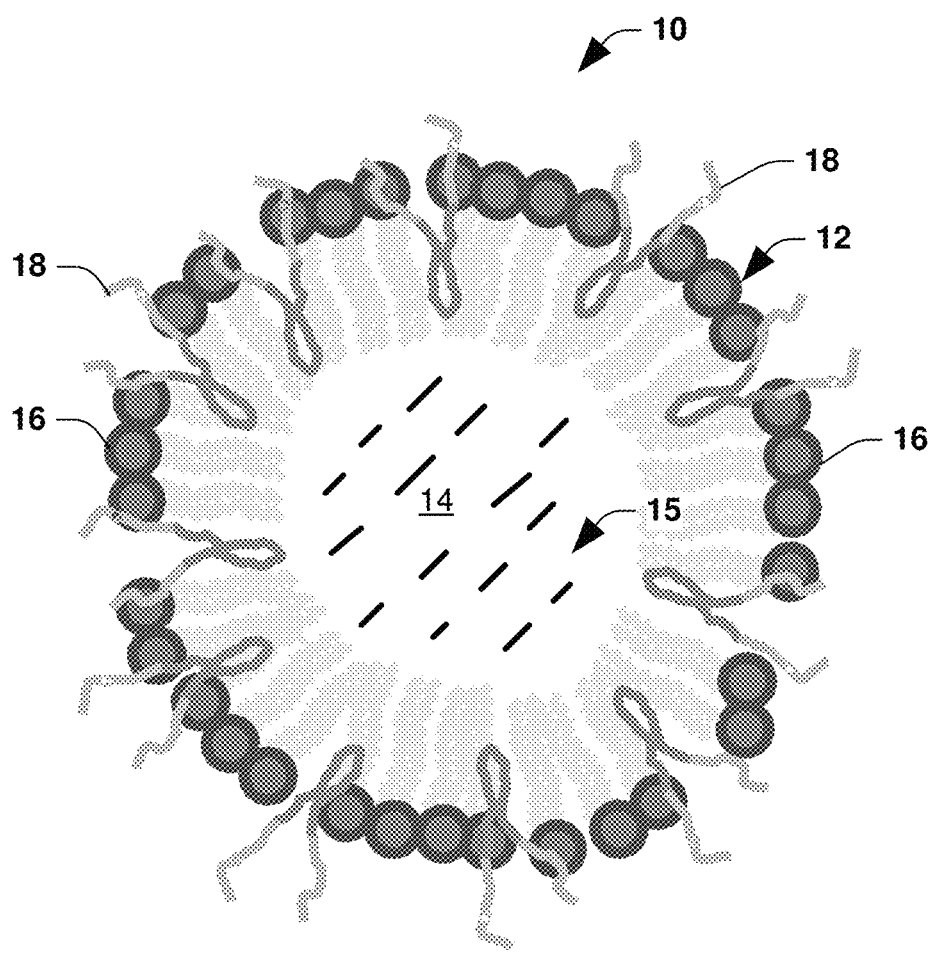
FIG. 1 is a schematic illustration of a nanobubble in accordance with an aspect of the application.

All scientific and technical terms used in this application have meanings commonly used in the art unless otherwise specified. The definitions provided herein are to facilitate understanding of certain terms used frequently herein and are not meant to limit the scope of the application.

As used herein, the term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" can refer to an abnormal mass or population of cells that result from excessive cell division, whether malignant or benign, and all pre-cancerous and cancerous cells and tissues.

As used herein, the terms "treating" or "treatment" of a disease (e.g., a neoplastic disorder) can refer to executing a treatment protocol to eradicate at least one neoplastic cell. Thus, "treating" or "treatment" does not require complete eradication of neoplastic cells.

As used herein, the term "polymer" can refer to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

As used herein, the term "block copolymer" can refer to a polymer in which adjacent polymer segments or blocks are different, i.e., each block comprises a unit derived from a different characteristic species of monomer or has a different composition of units.

As used herein, the term "poloxamer" can refer to a series of non-ionic triblock copolymers comprised of ethylene oxide and propylene oxide. Poloxamers are synthesized by the sequential addition of propylene oxide, followed by ethylene oxide, to propylene glycol. The poly(oxyethylene) segment is hydrophilic and the poly(oxypropylene) segment is hydrophobic. The molecular weight of poloxamers may range from 1000 to greater than 16000. The basic structure of a poloxamer is HO—$(C_2H_4O)_a(C_3H_6O)_b(C_2H_4O)_a$—H, where "a" and "b" represent repeating units of ethylene oxide and propylene oxide, respectively.

As used herein, the term "poloxamine" can refer to a polyalkoxylated symmetrical block copolymer prepared from an ethylene diamine initiator. Poloxamines are synthesized using the same sequential order of addition of alkylene oxides as used to synthesize poloxamers. Structurally, the poloxamines include four alkylene oxide chains and two tertiary nitrogen atoms, at least one of which is capable of forming a quaternary salt. Poloxamines are also terminated by primary hydroxyl groups.

As used herein, the term "meroxapol" can refer to a symmetrical block copolymer consisting of a core of polyethylene glycol (PEG) polyoxypropylated to both its terminal hydroxyl groups, i.e., conforming to the general type $(PPG)_x$-$(PEG)_y$-$(PPG)_x$, wherein "x" and "y" represent repeating units of PPG and PEG, respectively, and being formed by an ethylene glycol initiator. As opposed to the poloxamers, which are terminated by two primary hydroxyl groups, meroxapols have secondary hydroxyl groups at the ends and the hydrophobe is split in two, each half on the outside of the surfactant.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment.

This application relates to stabilized nanobubbles for diagnostic, therapeutic, and/or theranostic applications. The stabilized nanobubbles can be used as multifunctional platforms for molecular imaging, drug therapy, gene therapy, chemotherapy, and/or anti-microbial applications. It was found that nonionic triblock copolymers (e.g., poloxamers) when combined with lipids can form nanobubble contrast agents that when administered to a subject with cancer are clearly visible on ultrasound yet sufficiently small to move beyond leaky tumor vasculature, permitting greatly expanding molecular imaging capabilities of ultrasound at clinically relevant frequencies (e.g., 1 to 20 MHz).

The membranes of the stabilized nanobubbles described herein are tightly packed permitting a smaller size than traditionally formed microbubbles. Particle diameter has been the most widely accepted factor, which governs the resonant frequency of the bubble and its visibility with ultrasound. Typically, smaller bubbles vibrate faster, making them extremely difficult to detect with clinically relevant ultrasound frequencies. The stabilized nanobubbles described herein, however, are much more flexible than traditionally formed microbubbles as result of the nonionic triblock copolymer, which acts as a linker packed between lipids. This added flexibility of the nanobubbles reduces the resonant frequency or signal echogenicity to a point that make the nanobubbles detectable at frequencies as low as (1 MHz, e.g., 3.5 MHz) making the nanobubbles comparable to clinical agents but with the added benefit of small size.

Additionally, the nonionic triblock copolymers used in the formation of the stabilized nanobubbles can substantially decrease intracellular adenosine-5'-triphosphate (ATP) and heat shock protein HSP expression (e.g., HSP 70) when the nanobubbles are administered to cells subjected to stress sufficient to induce expression of HSP. Exposure to or application of stress and ATP depletion can also concomitantly cause intracellular HSP to remain bound to denaturing proteins rendering the indefinitely-bound HSP, an intracellular obstruction, thereby leading to cell death. Nanobubbles described herein can therefore sensitize neoplastic cells, such as tumor cells and cancer cells, as well as microorganisms, such as bacteria, viruses, fungi, and parasites, to cellular stress and induce apoptosis in the neoplastic cells or microorganisms.

Moreover, the lipid shell of the nanobubble allows therapeutic agents and targeting moieties to be linked to, conjugated to, or encapsulated by the nanobubble. This permits the nanobubbles to be used as delivery vehicles in therapeutic applications as well as provides active targeting of the nanobubbles to the tissue or cells being treated.

FIG. 1 illustrates a stabilized nanobubble 10 in accordance with one aspect of the application. The nanobubble 10 can include a membrane or shell 12 that defines an internal void 14. The internal void can include at least one gas 15. The membrane or shell 12 can include at least one type of lipid 16 and at least one type of nonionic triblock copolymer 18 that is effective in controlling and/or reducing the size of the lipid nanobubbles 10 without compromising nanobubble stability and in vitro and in vivo echogenicity.

"Nanobubble stability" can generally refer to the ability of the nanobubble to maintain its size in vitro and/or in vivo over time. For example, the nanobubble can maintain its size in vitro and/or in vivo over the course of minutes, days, weeks, or years. Additionally, nanobubble stability can refer to the polydispersity and/or zeta potential of the nanobubble. Polydispersity can refer to size distribution of the bubbles in solution, and zeta potential provides information on the stability of particle in suspension and is a function of particle surface charge. Nanobubbles described herein can have a polydispersity value of between about 0.1 and about 0.5, and a zeta potential of between about −30 mV and about −70 mV.

Figure 2:
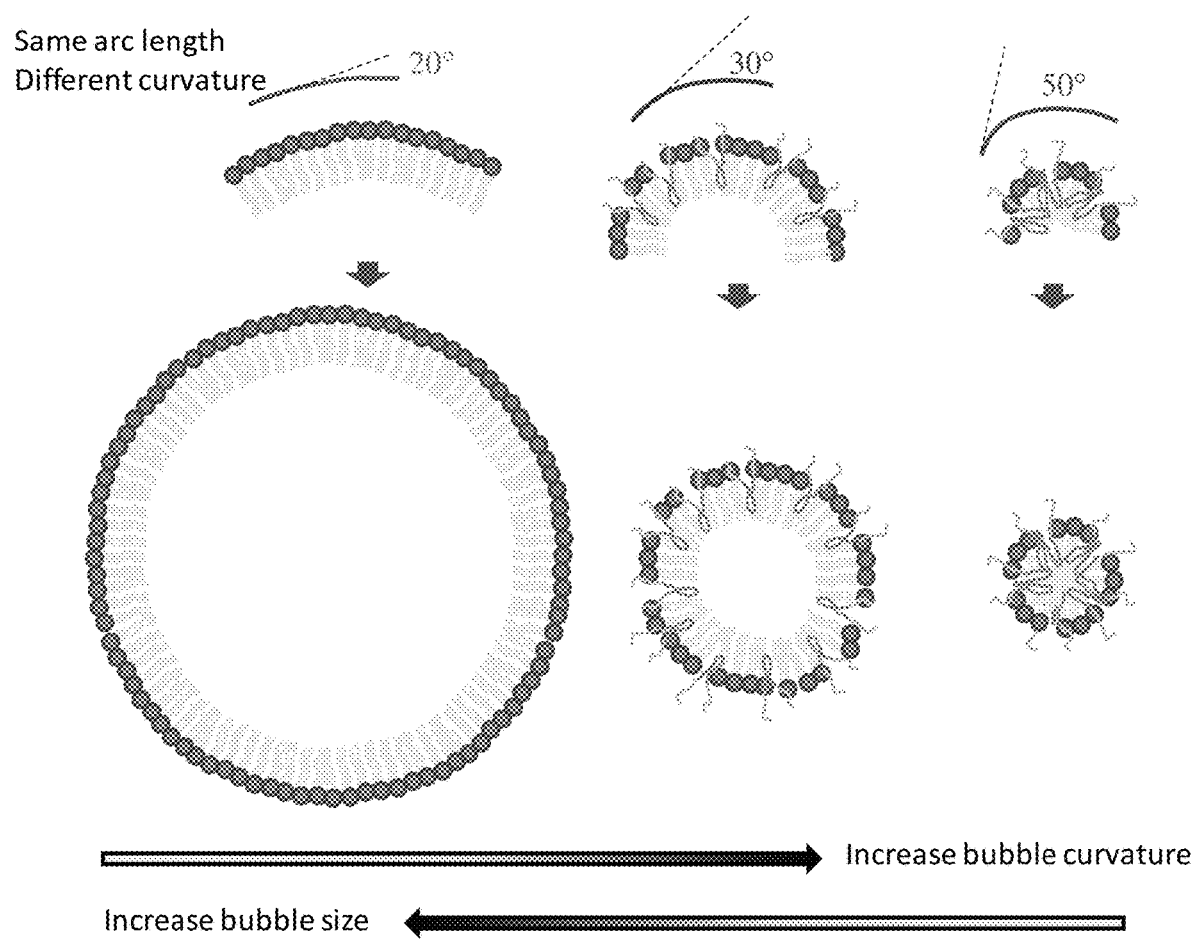
FIG. 2 is a schematic illustration of a proposed mechanism of lipid bubble size modulation by poloxamer in accordance with an aspect of the application.

The nonionic triblock copolymers (e.g., poloxamers) can change the packing of the lipids in the nanobubble shell and allow the nanobubble size (diameter) to be tailored to as small as about 50 nm. As illustrated in FIG. 2, it is believed the nonionic triblock copolymers can reduce the nanobubble shell by increasing the lipid shell curvature without compromising bubble stability. At the same arc length the higher the bubble curvature, the smaller the bubble size. As illustrated in FIG. 3, the nonionic triblock copolymer also enables a tighter packing but greater expansion (flexibility) of the lipid shell. Bubble resonance frequency is inversely proportional to bubble radius and related to shell elasticity, i.e., the more elastic the shell the lower the frequency. Therefore, the increase flexibility of the nanobubbles provided by the nonionic triblock copolymer leads to resonance at lower frequencies and highly echogenic bubbles.

In some embodiments, the nanobubble can have a size that facilitates extravasation of the nanobubble in cancer therapy or diagnosis. For example, the nanobubble can have a size (diameter) of about 50 nm to about 800 nm (e.g., about 50 nm to about 400 nm), depending upon the particular nonionic triblock copolymer and the method used to form the nanobubble (described in greater detail below).

The at least one lipid comprising the membrane or shell can include any naturally-occurring, synthetic or semi-synthetic (i.e., modified natural) moiety that is generally amphipathic (i.e., including a hydrophilic component and a hydrophobic component). Examples of lipids can include fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The at least one lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof. In one example of the application, the membrane can include a mixture of DPPA, DPPE and DPPC.

In some embodiments, the at least one nonionic triblock copolymer used to form the membrane can include an amphiphilic surfactant, such as a poloxamer, poloxamine, meroxapol, and/or combination thereof. In one example, the at least one nonionic triblock copolymer can comprise a poloxamer. The poloxamer can include any one or combination of a series of block copolymers of ethylene oxide and propylene oxide. The poly(oxyethylene) (PEO) and poly (oxypropylene) (PPO) segments may be hydrophilic and hydrophobic, respectively. The poloxamer may be a liquid, a paste, or a solid, and may have a molecular weight that ranges, for example, from about 1000 Daltons to about 3000 Daltons, although poloxamers having molecular weights greater or less than the these molecular weights can potentially be used. The concentration of nonionic triblock copolymer in the lipid nanobubble can be about 0.06 mg/ml to about 1 mg/ml.

The basic chemical formula of the poloxamer may be $HO—(C_2H_4O)_a(C_3H_6O)_b(C_2H_4O)_a—H$, where "a" and "b" represent repeating units of PEO and PPO, respectively. The ratio of a:b can be between about 1:10 and about 4:15. In one example, the poloxamer may have the chemical formula of $HO—(C_2H_4O)_2(C_3H_6O)_{31}(C_2H_4O)_2—H$. In another example of the present invention, the poloxamer may have the chemical formula of $HO—(C_2H_4O)_3(C_3H_6O)_{43}(C_2H_4O)_3—H$.

The poloxamer may be commercially available under various trade names including, for example, LUTROL, PLURONIC, SYNPERONIC (ICI), EMKALYX, PLURACARE, and PLURODAC. Examples of the PLURONIC series can include, but are not limited to, PLURONIC L81 (avg. $M_w$: 2750), PLURONIC L61 (avg. $M_w$: 2000), PLURONIC L72 (avg. $M_w$: 2750), PLURONIC L62 (avg. $M_w$: 2500), PLURONIC L42 (avg. $M_w$: 1630), PLURONIC L63 (avg. $M_w$: 2650), PLURONIC L43 (avg. $M_w$: 1850), PLURONIC L64 (avg. $M_w$: 2900), PLURONIC L44 (avg. $M_w$: 2200), and PLURONIC L35 (avg. $M_w$: 1900). Other commercially available poloxamers can include compounds that are block copolymers of polyethylene and polypropylene glycol, such as SYNPERONIC L121, SYNPERONIC L122, SYNPERONIC P104, SYNPERONIC P105, SYNPERONIC P123, SYNPERONIC P85, SYNPERONIC P94, and compounds that are nonylphenyl polyethylene glycol, such as SYNPERONIC NP10, SYNPERONIC NP30 and SYNPERONIC NP5.

In another aspect of the application, the at least one nonionic triblock copolymer can comprise a poloxamine. The poloxamine can include a polyalkoxylated symmetrical block copolymer prepared from an ethylene diamine initiator. Poloxamines are synthesized using the same sequential order of addition of alkylene oxides as used to synthesize poloxamers. Structurally, the poloxamines can include four alkylene oxide chains and two tertiary nitrogen atoms, at least one of which is capable of forming a quaternary salt. Poloxamines can also be terminated by primary hydroxyl groups. Examples of poloxamines can include, but are not limited to, the TETRONIC and/or TETRONIC R series produced by BASF. For example, poloxamines can include TETRONIC 904, TETRONIC 908, TETRONIC 1107, TETRONIC 90R4, TETRONIC 1304, TETRONIC 1307 and TETRONIC T1501.

In another aspect of the application, the at least one nonionic triblock copolymer can include a meroxapol. Meroxapols can include a symmetrical block copolymer consisting of a core of PEG polyoxypropylated to both its terminal hydroxyl groups, i.e., conforming to the general type $(PPG)_x-(PEG)_y-(PPG)_x$, and being formed by an ethylene glycol initiator. Examples of meroxapols can include, but are not limited to, MEROXAPOL 105, MEROXAPOL 108, MEROXAPOL 172, MEROXAPOL 174, MEROXAPOL 252, MEROXAPOL 254, MEROXAPOL 258 and MEROXAPOL 311.

The membrane defining the nanobubble can be concentric or otherwise and have a unilamellar configuration (i.e., comprised of one monolayer or bilayer), an oligolamellar configuration (i.e., comprised of about two or about three monolayers or bilayers), or a multilamellar configuration (i.e., comprised of more than about three monolayers or bilayers). The membrane can be substantially solid (uniform), porous, or semi-porous.

The internal void defined by the membrane can include at least one gas. The gas can have a low solubility in water and be, for example, a perfluorocarbon, such as perfluoropropane (e.g., octafluoropropane). The internal void can also include other gases, such as carbon dioxide, air, nitrogen, and helium.

The stabilized nanobubbles can also include other materials, such as liquids, oils, bioactive agents, diagnostic agents, and/or therapeutic agents. The materials can be encapsulated by the membrane and/or linked or conjugated to the membrane.

Bioactive agents encapsulated by and/or linked to the membrane can include any substance capable of exerting a biological effect in vitro and/or in vivo. Examples of bioactive agents can include, but are not limited to, chemotherapeutic agents, biologically active ligands, small molecules, DNA fragments, DNA plasmids, interfering RNA molecules, such as siRNAs, oligonucleotides, and DNA encoding for shRNA. Diagnostic agents can include any substance that may be used for imaging a region of interest (ROI) in a subject and/or diagnosing the presence or absence of a disease or diseased tissue in a subject. Therapeutic agents can refer to any therapeutic or prophylactic agent used in the treatment (including the prevention, diagnosis, alleviation, or cure) of a malady, affliction, condition, disease or injury in a subject. It will be appreciated that the membrane can additionally or optionally include proteins, carbohydrates, polymers, surfactants, and/or other membrane stabilizing materials, any one or combination of which may be natural, synthetic, or semi-synthetic.

In some embodiments, the bioactive agent can include a therapeutic agent, such as a chemotherapeutic agent, an anti-proliferative agent, an anti-microbial agent, a biocidal agent, and/or a biostatic agent. The therapeutic agent can be encapsulated by and/or linked to the membrane of the nanobubble.

In another aspect of the application, the membrane can additionally or optionally include at least one targeting moiety that is capable of targeting and/or adhering the nanobubble to a cell or tissue of interest. In some embodiments, the targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as CA-125 receptor, epidermal growth factor receptor, and transferrin receptor. The targeting moiety can interact with the biomarkers through non-covalent binding, covalent binding, hydrogen binding, van der Waals forces, ionic bonds, hydrophobic interactions, electrostatic interaction, and/or combinations thereof.

The targeting moiety can include, but is not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can comprise an antibody, such as a monoclonal antibody, a polyclonal antibody, or a humanized antibody, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating antibodies. These methods typically include the step of immunization of animals, typically mice, with a desired immunogen (e.g., a desired target molecule or fragment thereof). Once the mice have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

The targeting moiety need not originate from a biological source. The targeting moiety may, for example, be screened from a combinatorial library of synthetic peptides. One such method is described in U.S. Pat. No. 5,948,635, incorporated herein by reference, which describes the production of phagemid libraries having random amino acid insertions in the pIII gene of M13. These phage may be clonally amplified by affinity selection.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moiety may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. Also, transgenic mice, or other mammals, may be used to express humanized antibodies. Such humanization may be partial or complete.

In certain embodiments, a targeting moiety as described herein may comprise a homing peptide, which selectively directs the nanobubble to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 56,226,999; 6,068,829; 6,174,687; 6,180,084; 6,232, 287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In other embodiments, the targeting moiety may comprise a ligand molecule, including, for example, ligands which naturally recognize a specific desired receptor of a target cell. Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated that mimic those residues, which facilitate the interaction. Such mimetics may then be used as a targeting moiety to deliver the nanobubble to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

By way of example, where the cell targeted comprises an ovarian cancer cell, the targeting moiety can comprise an antibody or peptide to human CA-125R. Over expression of CA-125 has implication in ovarian cancer cells. Alternatively, where the cell targeted comprises a malignant cancer, such as glioblastoma, the targeting moiety can comprise an antibody or peptide to extracellular growth factor receptor (EGFR) and/or human transferrin receptor (TfR). Overexpression of EGFR and TfR has been implicated in the malignant phenotype of tumor cells. The overexpression of these receptors also leads to activation of other genes that promote cancer growth through such means as invasion and metastasis, as well as resistance to chemotherapy and radiotherapy. The imaging of cancer cells expressing EGFR and TfR can provide a molecular signature of the malignancy or progression of such cells.

In some embodiments, the nanobubbles can include a linker to link the targeting moiety and/or bioactive agent to the membrane of the nanobubble. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

Figure 4:
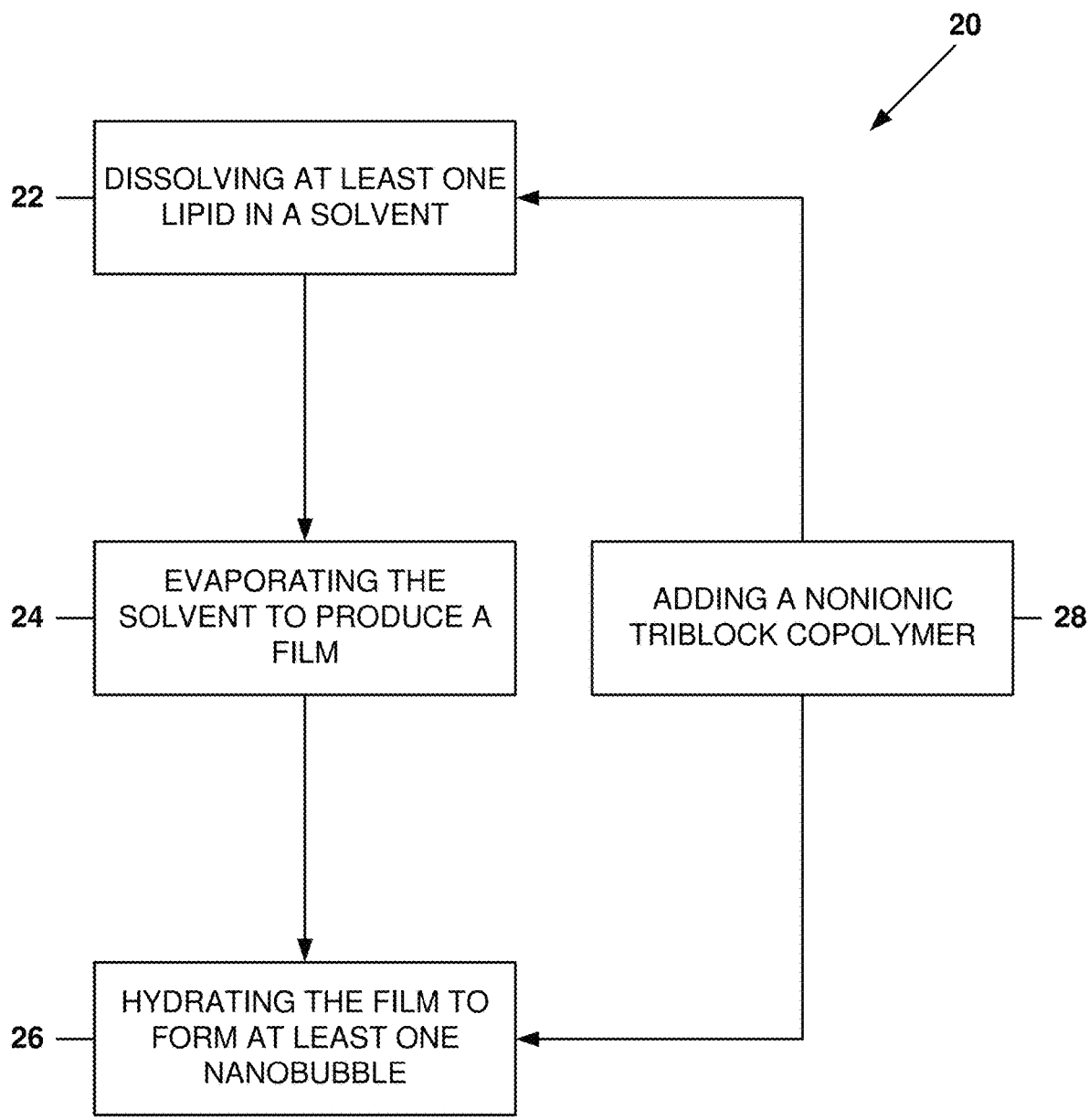
FIG. 4 is a flow diagram illustrating a method for forming a composition comprising at least one stabilized nanobubble in accordance with an aspect of the application.

FIG. 4 is a flow diagram illustrating a method 20 of forming a composition comprising at least one stabilized nanobubble. Although previous methodologies have been developed to reduce bubble size, most of these strategies involve manipulations of microbubbles post formation, such as gradient separation by gravitational forces or by physical filtration or floatation. While effective for selecting nano-sized bubbles, these methods introduce potential for sample contamination, reduce bubble yield and stability, and waste stock materials in addition to being labor intensive. Unlike the post formation methods of the prior art, the method described herein can be used to form nanobubbles without any manipulation of the bubbles post formation and thereby avoid or mitigate the potential for sample contamination, reduced bubble yield and stability, waste of stock materials, and labor intensive.

At Step 22 of the method 20, at least one lipid can be dissolved in a solvent to produce a lipid-solvent solution. The lipid(s) dissolved in the solvent can include any one or combination of those described above. It will be appreciated that other materials can be dissolved in the solvent to stabilize the membrane, such as proteins, carbohydrates, polymers, surfactants, and/or other membrane stabilizing materials. The solvent can include any organic solvent, such as chloroform, methylene chloride, ethylene chloride, ethylene dichloride, ethyl acetate, methylchloroform, tetrahydrofuran or benzene. In one example of the present invention, DPPC, DPPA, and DPPE can be dissolved in the chloroform.

After producing the lipid-solvent solution, the solvent can be evaporated at a temperature and for a time sufficient to form a film (Step 24). For example, the lipid-solvent solution can be placed in an open container (e.g., an evaporating dish, beaker, vial, etc.) and then set on a heat source (e.g., incubator, steam bath, hot plate, heating mantle, sand bath, etc.) at a temperature and for a time sufficient to evaporate the solvent and form the film.

At Step 26, the resultant film can be hydrated to form at least one lipid vesicle. The term "vesicle" can refer to any entity that is generally characterized by the presence of one or more walls or membranes that define one or more internal voids. The film can be hydrated by contacting an amount of at least one buffer solution (e.g., about 1×PBS) with an organic compound (e.g., glycerol). The hydration buffer/organic compound solution can then be placed in a container (e.g., a vial) and stirred or shaken at a temperature and for a time sufficient to produce at least one lipid vesicle. In one example, a lipid-solvent solution comprising DPPC/DPPA/DPPE dissolved in chloroform can be contacted with a hydration PBS/glycerol solution, placed in a vial, and then placed in an incubator-shaker at about 37° C. and at about 120 rpm for about 60 minutes.

At Step 28, at least one nonionic triblock polymer can be added to the hydration/organic compound solution to form the nanobubble. As shown in FIG. 4, the at least one nonionic triblock copolymer can be added at Step 22 or Step 26 of the method. The at least one nonionic triblock polymer can be added at a concentration and/or at a lipid: nonionic triblock polymer ratio effective to control the size of the nanobubble and impart the nanobubble with in vitro and in vivo echogenicity. In one example, PLURONIC L61 can be added to the hydration buffer/organic compound solution (Step 26) at a concentration of between about 0.1 mg/mL and about 1 mg/mL and at a lipid:PLURONIC L61 ratio of about 30:1 to about 40:1. Alternatively, PLURONIC L81 can be added to the hydration buffer/organic compound solution (Step 26) at a concentration of between about 0.06 mg/mL and about 1 mg/mL and at a lipid:PLURONIC L81 ratio of about 40:1 to about 50:1. Following the addition of the at least one nonionic triblock copolymer, the resultant solution can then be shaken or stirred for a time (e.g., about 45 seconds) sufficient to form the nanobubble.

As noted above, size control of the nanobubble can be dependent on the molecular weight, hydrophobicity, and PPO block length of the at least one nonionic triblock copolymer used to form the nanobubble. Where about 0.6 mg/mL of PLURONIC L61 is used to form the nanobubble, for example, the nanobubble produced by the method can have a size (diameter) of between about 100 nm and 600 nm. Alternatively, where about 0.6 mg/mL of PLURONIC L81 is used to form the nanobubble, the nanobubble produced by the method can have a size (diameter) of between about 300 nm and 500 nm. After forming the composition comprising at least one nanobubble, the composition can be stored (e.g., by placing the composition on ice or under refrigeration at 4° C.) or immediately prepared for use.

The stabilized nanobubble composition so formed can be administered to a subject for diagnostic, therapeutic, and/or theranostic applications. In some embodiments, the nanobubbles can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external.

In some embodiments, the nanobubbles used to image the ROI can be formulated such that the internal void of at least one of the nanobubbles includes at least one contrast agent. For example, a contrast agent (in either liquid or gaseous form) can be contacted with the hydrated lipid/nonionic triblock copolymer solution under conditions effective to entrap the contrast agent in the internal void of the nanobubble. For instance, sealed vials containing a lipid 1,2-dipalmitoyl-sn-glycero-3-phosphocholine/dipalmitoyl-sn-glycero-3-phosphoethanolamine/dipalmitoyl-sn-glycero-3-phosphate (DPPC/DPPA/DPPE)/poloxamer solution can have the air withdrawn by a syringe and then octafluoropropane added until the pressure in the vial is equalized. Other examples of contrast agents (besides octafluoropropane) that may be incorporated into the nanobubbles are known in the art and can include stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules.

Since nanobubble size may influence biodistribution, the size of the nanobubbles can be selected depending upon the region of interest (ROI) of the subject. For a ROI comprising an organ (e.g., a liver or kidney) the size of the nanobubbles may be greater than for a ROI comprising tumor tissue. Where the ROI comprises, for example, tumor tissue and differentiation between the tumor tissue and normal or healthy tissue is sought, smaller nanobubbles may be needed to penetrate the smaller venuoles and capillaries comprising the tumor tissue. It should be appreciated that the nanobubbles can comprise additional constituents, such as targeting ligands to facilitate homing of the nanobubbles to the ROI.

The nanobubble composition can be administered to the subject via any known route, such as via an intravenous injection. By way of example, a composition comprising a plurality of octafluoropropane-containing nanobubbles can be intravenously administered to a subject that is known to or suspected of having a tumor.

At least one image of the ROI can be generated using an imaging modality. The imaging modality can include one or combination of known imaging techniques capable of visualizing the nanobubbles. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET). The imaging modality can then be operated to generate a visible image of the ROI. In a subject known to or suspected of having a tumor, for example, an ultrasonic transducer can be applied to at least a portion of the ROI to image the target tissue. A visible image of the tumor can then be obtained, such that the presence, absence, and/or extent of a particular neoplastic disorder can be ascertained. It will be appreciated that the imaging modality may be used to generate a baseline image prior to administration of the composition. In this case, the baseline and post-administration images can be compared to ascertain the presence, absence, and/or extent of a particular disease or condition.

In other embodiments, the nanobubbles can be administered to a subject to treat and/or image a neoplastic disease in subject. Neoplastic diseases treatable by the present invention can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells.

A composition comprising the stabilized nanobubbles can be formulated for administration (e.g., injection) to a subject diagnosed with at least one neoplastic disorder. The nanobubbles can be formulated according to method as described above and include, for example, at least one therapeutic agent or bioactive agent as well as targeting moiety to target the neoplastic cells.

By way of example, the stabilized nanobubbles can be targeted to ovarian cancer cells by conjugating a ligand that this is specific for the CA-125 receptor that is over expressed on ovarian cancer cells. The targeted stabilized nanobubbles can be formulated with at least one lipid that is conjugated to biotin. The nanobubbles can then be combined with streptavidin and a biotinylated anti-CA-125 antibody (e.g., MUC16, ab90346), which will then become conjugated to biotin of the lipid.

The location(s) where the nanobubble composition is administered to the subject may be determined based on the subject's individual need, such as the location of the neoplastic cells (e.g., the position of a tumor, the size of a tumor, and the location of a tumor on or near a particular organ). For example, the composition may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

Since nanobubble size may influence biodistribution, the size of the nanobubbles can be selected depending on the neoplastic disorder being imaged and/or treated. Where the neoplastic disorder comprises tumor tissue, smaller nanobubbles may be needed to penetrate the smaller venuoles and capillaries comprising the tumor tissue.

Optionally, the stabilized nanobubbles can be administered to neoplastic cells in combination with an applied stress effective to induce heat shock protein (HSP) expression in the neoplastic cells. In this method, the composition of stabilized nanobubbles may be administered to the neoplastic cells at amount effective to sensitize the neoplastic cells to the stress. It was found that the nonionic triblock copolymers (e.g., pluronics) used to stabilize the nanobubbles can substantially decrease intracellular adenosine-5'-triphosphate (ATP) and HSP expression (e.g., HSP 70) in neoplastic cells subjected to stress sufficient to induce expression of heat shock proteins (HSP). Exposure to or application of stress and ATP depletion can also concomitantly cause intracellular HSP to remain bound to denaturing proteins rendering the indefinitely-bound HSP an intracellular obstruction thereby leading to cell death.

Neoplastic cells can be pretreated with a composition comprising the nanobubbles prior to exposure to stress. For example, a composition comprising the nanobubbles may be administered to a neoplastic cell for an amount of time before the cell is exposed to stress. Alternatively, a composition comprising the nanobubbles can be administered concomitantly with the exposure of the cell or microorganism to stress.

In some embodiments, the stress applied to a cell can include radiotherapy, radiation, thermal stress or thermal therapy (e.g., hyperthermia), and stress induced by inflammation, anti-proliferative agents or chemotherapeutic agents.

In some aspects, a neoplastic can be exposed to thermal stress or thermal therapy, such as hyperthermia. For example, a neoplastic cell can be exposed to heat via focused ultrasound (FUS or HIFU), radiofrequency, infrared sauna, microwave heating, induction heating, magnetic hyperthermia, infusion of warmed liquids, or direct application of heat.

The exposure to heat can include local hyperthermia. Local hyperthermia heats a very small area, usually the tumor itself. In some instances, the goal is to kill the tumor by "cooking" it, without damaging surrounding healthy tissue. The heat may be created with microwave, radiofrequency, ultrasound energy or using magnetic hyperthermia. Depending on the location of the tumor, the heat may be applied to the surface of the body, inside normal body cavities, or deep in tissue through the use of needles or probes. One relatively common type is radiofrequency ablation of small tumors. This is easiest to achieve when the tumor is on a superficial part of the body, which is called superficial hyperthermia, or when needles or probes are inserted directly into the tumor, which is called interstitial hyperthermia.

Regional hyperthermia heats a larger part of the body, such as an entire organ or limb. Usually, the goal is to weaken cancer cells so that they are more likely to be killed by radiation and chemotherapeutic medications. This may use the same techniques as local hyperthermia treatment, or it may rely on blood perfusion. In blood perfusion, the patient's blood is removed from the body, heated up, and returned to blood vessels that lead directly through the desired body part. Normally, chemotherapy drugs are infused at the same time. One specialized type of this approach is continuous hyperthermic peritoneal perfusion (CHPP), which is used to treat difficult cancers within the peritoneal cavity (the abdomen), including primary peritoneal mesothelioma and stomach cancer where heated chemotherapy drugs are pumped directly into the peritoneal cavity to kill the cancer cell.

In some aspects of the application, exposure to thermal stress or thermal therapy can include exposure to sub-lethal heat. For example, a hyperthermia modality may heat a cancer cell to much lower therapeutic temperatures (in general <45° C.) compared to other tissue ablation techniques. One modality of thermotherapy is termed "hyperthermia" therapy, an approach to thermal treatment at temperatures elevated within somewhat narrow confines above normal body temperature. For instance, the elevation above a normal body temperature of 37° C. typically will fall within a range of 42° C. to 45° C.

A variety of approaches toward intra-body localized heat applications can be utilized to expose the neoplastic cells to sub-lethal heat. For example, intra-body exposure to localized heat may be based upon the application of microwave energy (see U.S. Pat. No. 4,138,998); the application of acoustic wave-based systems (ultrasound); and the application of electric fields at RF frequencies from transmitting antenna arrays including an application subset utilizing inductive systems driven at relatively lower frequencies below the RF realm.

In some aspects, the neoplastic cell can be exposed to radiation therapy or radiotherapy. Radiation therapy may include both "sealed" and "unsealed" sources of therapeutic radiation including, but not limited to, radiation therapy, brachytherapy, endovascular radioembolization and targeted radionuclide therapies, such as radioiodine ablation, peptide targeted radiotherapy, radioimmunotherapy, and radiotherapy enhanced nanoparticles.

In other aspects, a chemotherapeutic agent or anti-proliferative agent may be administered to the subject before, during, or after sensitizing the neoplastic cells with the stabilized nanobubbles. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which can administered in combination with the stabilized nanobubbles.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination with the stabilized nanobubbles consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the stabilized nanobubbles consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the stabilized nanobubbles consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the stabilized nanobubbles consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer.

5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the stabilized nanobubbles of hormonal agents. Examples of hormonal-type anti-proliferative agents that may be used in the present invention include, but are not limited to Abarelix; Abbott A-84861; Abiraterone acetate; Aminoglutethimide; anastrozole; Asta *Medica* AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the stabilized nanobubbles consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The stabilized nanobubbles described herein can allow the combination of any of the above noted therapeutic agents and therapies to be administered at a low dose, that is, at a dose lower than has been conventionally used in clinical situations.

A benefit of lowering the dose of the combination therapeutic agents and therapies administered to a subject includes a decrease in the incidence of adverse effects associated with higher dosages. For example, by the lowering the dosage of a chemotherapeutic agent, such as 5-FU, a reduction in the frequency and the severity of nausea and vomiting will result when compared to that observed at higher dosages. Similar benefits are contemplated for the compounds, compositions, agents and therapies in combination with the nanobubbles.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Additionally, given that over-expression of HSPs have been linked with drug resistant infections, it is further contemplated herein that applications of stabilized nanobubbles described above can include integration with traditional antimicrobial agents rendering them more effective. Accordingly, this application also relates to compositions and methods of sensitizing microorganisms, such as bacteria, fungi, viruses, and parasites to antimicrobial agents.

It is contemplated herein that composition comprising the stabilized nanobubbles may also be integrated into routine cleaning and sterilization supplies utilized in the healthcare setting such as disinfectants and antiseptics. Many hospital organisms such as MRSA and *Pseudomonas* are often resistant to standard agents and using the stabilized nanobubbles within these agents may render them more effective and decrease rates of nosocomial infection. For example, a composition comprising stabilized nanobubbles described herein may be added to a disinfectant or antiseptic at an amount effective to potentiate the biocidal or biostatic properties of antimicrobial agent.

Therefore, another aspect of the application relates to an antimicrobial composition that includes at least one biocidal agent or biostatic agent that can induce or promote HSP expression in a microorganism and an amount of the stabilized nanobubbles effective to substantially inhibit HSP expression and/or function induced or promoted by the biocidal agent or biostatic agent in the microorganism.

Biocidal agents and biostatic agents that can be used in the methods and materials described herein include agents that kill microbes as well as agents that simply inhibit their growth or accumulation. For health reasons, biocidal or biostatic agents that inhibit the growth of microbes are preferably used for materials that are to be used in, for example, consumer products.

Biocidal agents and biostatic agents can include antimicrobial agents, anti-fungals, antibiotics, anti-parasitics, disinfective agents, sanitizing agents, and chemisterillant (sterilant) agents, such as those listed in United States Pharmacopeial Convention, Inc. United States Pharmacopeia 28-National Formulary 23, Rockville, Md.: US Pharmacopeial Convention, Inc.; 2004: 61-62, 227-228, 439-441, 943-944, 972, 1029, 1077, 1532-1533, 1601, 1786, 2964-2965.

Examples of biocidal agents and biostatic agents include: alcohol, glycol, aldehyde and acids; iodophors such as iodine or povidone iodine; oxidizing agents, such as hydrogen peroxide or sodium hypochlorite; phenols and related compounds, such as hexacholophene; surface-active agents, such as chlorohexidine and quaternarium ammonium and derivatives.

Additional examples of biocidal agents and biostatic agents that can be used in the materials and methods described herein include, but are not limited to, phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic biocidal agents and biostatic agents that can be used include, but are not limited to: phenol; 2-methyl phenol; 3-methyl phenol; 4-methyl phenol; 4-ethyl phenol; 2,4dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n hexyl phenol; 4-n-heptyl phenol; mono- and poly-alkyl and aromatic halophenols; p-chloroplienol; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chiorophenol, 6-ethyl-3methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2 methylphenol; 5-methyl-2-pentylphenol; 4-isopropyl-3methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as biocidal agents and biostatic agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2, 4-dihydroxydiphenyl methane.

Specific bisphenolic agents that can be used include, but are not limited to: 2,2'-methylene bis-(4-chlorophenol); 2,4, 4'-trichloro-2'hydroxy-diphenyl ether, which is sold by Ciba Geigy, Florham Park, N.J. under the tradename Triclosan; 2,2'methylene bis-(3,4,6-trichlorophenol); 2,2'-methylene bis(4-chloro-6-bromophenol); bis-(2-hydroxy 3,5dichlorophenyl) sulphide; and bis-(2-hydroxy-5chlorobenzyl) sulphide.

Specific benzoic esters (parabens) that can be used include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used include, but are not limited to: 3,4,4'trichlorocarbanilides, such as 3-(4-chlorophenyl)-1-(3,4dichlorphenyl) urea sold under the tradename Triclocarban by Ciba-Geigy, Florham Park, N.J.; 3-trifiuoromethyl-4,4'dichlorocarbanilide; and 3,3',4-trichlorocarbanilide. Specific polymeric antiviral and antimicrobial agents that can be used in the invention include, but are not limited to: polyhexamethylene biguanide hydrochloride; and poly (iminoimidocarbonyl iminoimidocarbonyl iminohexamethylene hydrochloride), which is sold under the tradename Vantocil IB.

Specific thazolines that can be used in the invention include, but are not limited to that sold under the tradename Micro-Check; and 2-n-octyl-4-isothiazolin-3-one, which is sold under the tradename Vinyzene IT-3000 DIDP. Specific trichloromethylthioimides that can be used in the invention include, but are not limited to: N-(trichloromethylthio) phthalimide, which is sold under the tradename Fungitrol®; and N-trichloromethylthio-4cyclohexene-1,2-dicarboximide, which is sold under the tradename Vancide.

Specific natural antimicrobial agents that can be used include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fieagrass; geranium; sandalwood; violet; cranberry; *eucalyptus*; vervain; peppermint; gum benzoin; basil; fennel; fir; balsam; menthol; ocmea origanuin; hydastis; carradensis; Berberidaceac daceae; Ratanhiae Zanga; and *Curcuma* Zanga. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used include, but are not limited to, salts of metals in groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. A preferred metal-ion based antimicrobial agent is sold under the tradename HealthShield®, and is manufactured by HealthShield Technology, Wakefield, Mass.

Specific broad-spectrum antimicrobial agents that can be used in the invention include, but are not limited to, those that are recited in other categories of antiviral or antimicrobial agents herein. Additional antiviral or antimicrobial agents that can be used in the compositions and methods described herein include, but are not limited to: pyrithiones, and in particular pyrithione-including zinc complexes such as that sold under the tradename Octopirox®; dimethyidimethylol hydantoin, which is sold under the trade name Glydant; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11; benzyl alcohol v2-bromo-2-nitropropane-1,3-diol, which is sold under the tradename Bronopol; formalin or formaldehyde; iodopropenyl butylcarbamate, which is sold under the tradename Polyphase P100; chloroacetamide; methanamine; methyldibromonitrile glutaronitrile (1,2-dibromo-2,4dicyanobutane), which is sold under the tradename Tektamer; glutaraldehyde; 5 bromo-5-nitro-1,3-dioxane, which is sold under the tradename Bronidox; phenethyl alcohol; o-phenylphenollsodium o-phenylphenol sodium hydroxymethylglycinate, which is sold under the tradename Suttocide A; polymethoxy bicyclic oxazolidine; which is sold under the tradename Nuosept C; dimethoxane; thimersal; dichlorobenzyl alcohol; captan; chlorphenenesin; dichlorophene; chlorbutanol; glyceryl laurate; halogenated diphenyl ethers; 2,4, 4'-trichloro-2'-hydroxy-diphenyl ether; and 2,2'dihydroxy-5, 5'-dibromo-diphenyl ether.

Additional antiviral and antimicrobial agents that can be used in the compositions and methods described herein include those disclosed by U.S. Pat. Nos. 3,141,321; 4,402, 959; 4,430,381; 4,533,435; 4,625,026; 4,736,467; 4,855, 139; 5,069,907; 5,091,102; 5,639,464; 5,853,883; 5,854, 147; 5,894,042; and 5,919,554, all of which are incorporated herein by reference.

It is further contemplated that compositions comprising the stabilized nanobubbles described herein can render over-the-counter consumables, such as mouthwash, toothpaste, and topical ointments, more effective in decreasing biological flora.

In addition, the stabilized nanobubbles can be used in making gels in situ, making them useful for drug delivery either alone or in combination with other drug delivery formulations. The stabilized nanobubbles can be used not only in a biodegradable and implantable system to deliver drugs, thermoactive agents, radionucleotides, or other biologics but would also augment their desired effects through sensitization as described above.

Therefore, another aspect of the application provides a method of treating a microbial infection in a subject. The method includes administering to the subject an antimicrobial agent and an amount of a composition comprising the stabilized nanobubbles effective to potentiate the biocidal or biostatic properties of the antimicrobial agent.

In some embodiments a stabilized nanobubble composition described herein can be administered to a subject concomitantly with an oral antibiotic pharmaceutical composition and the stabilized nanobubble composition is effective in potentiating the biocidal or biostatic of the oral antibiotic therapy.

Antibiotic agents administered in conjunction with stabilized nanobubble composition can include, but are not limited to aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cephaclor, cefprozil, cephadrine, cefamandole, cefonicid, ceforanide, cefuroxime, cefixime, cefoperazone, cefotaxime, cefpodoxime, ceftazidime, ceftibuten, ceftizoxime, ceftriaxone, cefepime, cefmetazole, cefotetan, cefoxitin, ciprofloxacin, clarithromycin, clindamycin, clofazimine, cloxacillin, co-trimoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, imipenem, isoniazid, levofloxacin, lomefloxacin, loracarbef, methicillin, methenamine, metronidazole, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulfacytine, sulfamerazine, sulfamethazine, sulfamethizole, sulfasalazine, sulfisoxazole, sulfapyrazine, sulfadiazine, sulfinethoxazole, sulfapyridine, ticarcillin, ticarcillin and potassium clavulanate, trimethoprim, trimetrexate, troleandomycin, vancomycin and mixtures thereof.

It will be appreciated that the stabilized nanobubbles can be used in other applications besides diagnostic, therapeutic, and theranostic applications described above. Nanobubble ultra sound contrast agents have shown great potential in areas of health including cardiovascular and eye diseases, as well as neuromusclular disorders such as Duschenne Muscular dystrophy. Inflammation has been associated with hypoxia. Nanobubbles can deliver oxygen to hypoxic cell and tissues and can be a potential treatment option. In addition, the early stage of atherosclerosis has been manifested with over-expressed intercellular adhesion molecule-1 (ICAM-1), an inflammatory marker. By including ICAM-1 recognizing monoclonal antibodies in the nanobubble membrane or shell, nanobubbles can recognize and adhere to intercellular adhesion molecule-1 (ICAM-1). These types of nanobubble formulations can be used to detect early stages of atherosclerosis, and can be effective in detecting acute cardiac transplant rejection.

Moreover, stabilized nanobubbles described herein can also be used for the treatment of Parkinson's disease. In this regard, the nanobubbles can be used to deliver apomorphine, a particularly beneficial but unstable drug for treating Parkinson's disease, through the blood brain barrier.

Although the use of nanobubbles in medicine is in an early development stage, it is possible that in the future, the applications of nanobubbles in medicine will be as far reaching if not more than that of microbubbles whose applications span across the areas of malignant, infectious, cardiovascular and autoimmune diseases.

The following example is for the purpose of illustration only and is not intended to limit the scope of the claims, which are appended hereto.

EXAMPLES

Example 1

In this Example, we present a novel strategy for formulation of nano-sized, echogenic lipid bubbles by incorporating the surfactant Pluronic, a triblock copolymer of ethylene oxide co-propylene oxide coethylene oxide into the formulation. Five Pluronics (L31, L61, L81, L64 and P85) with a range of molecular weights (Mw: 1100 to 4600 Da) were incorporated into the lipid shell either before or after lipid film hydration and before addition of perfluorocarbon gas. Results demonstrate that Pluronic-lipid interactions lead to a significantly reduced bubble size. Among the tested formulations, bubbles made with Pluronic L61 were the smallest with a mean hydrodynamic diameter of 207.9±74.7 nm compared to the 880.9±127.6 nm control bubbles. Pluronic L81 also significantly reduced bubble size to 406.8±21.0 nm. We conclude that Pluronic is effective in lipid bubble size control, and Pluronic Mw, HLB, and Pluronic/lipid ratio are critical determinants of the bubble size. Most importantly, our results have shown that although the bubbles are nano-sized, their stability, and in vitro and in vivo echogenicity are not compromised. The resulting nanobubbles may be better suited for contrast enhanced tumor imaging and subsequent therapeutic delivery.

Materials and Methods

Materials

Pluronic P85 and L61 were donated by BASF (Shreveport, La.). Other Pluronic products (Table 1) and glycerol were purchased from Sigma Aldrich (Milwaukee, Wis.). Octaflouropropane (C3F8) gas was purchased from American Gas Group (Toledo, Ohio). Dulbecco's phosphate buffered saline (PBS), was purchased from GIBCO (Grand Island, N.Y.). Lipids, 1,2-dipalmitoyl-sn-glycero-3-phosphocholine (DPPC; Mw: 734.05), 1,2-dipalmitoyl-sn-glycero-3-phosphoethanolamine (DPPE; Mw: 691.97), and 1,2-dipalmitoyl-sn-glycero-3-phosphate (DPPA; Mw: 670.88) in powder form were purchased from Avanti Polar Lipids Inc. (Pelham, Ala.) and used without further purification.

TABLE 1

Pluronic Information

| Pluronic | Formula | Mw (Da) | HLB | PO/EO ratio | CMC (M); CMC (wt %) |
|---|---|---|---|---|---|
| L31 | $EO_2$-$PO_{16}$-$EO_2$ | 1100 | 1-7 | 8 | N/A |
| L61 | $EO_2$-$PO_{31}$-$EO_2$ | 2000 | 1-7 | 13.6 | 1.1 × 10.4; 0.022 |
| L81 | $EO_3$-$PO_{43}$-$EO_3$ | 2750 | 1-7 | 13.7 | 2.3 × 10−5; 0.0063 |
| L64 | $EO_{13}$-$PO_{30}$-$EO_{13}$ | 2900 | 12-18 | 2.3 | 4.8 × 10−4; 0.14 |
| P85 | $EO_{26}$-$PO_{40}$-$EO_{26}$ | 4600 | 16 | 1.5 | 6.5 × 10−5; 0.03 |

Figure 5:
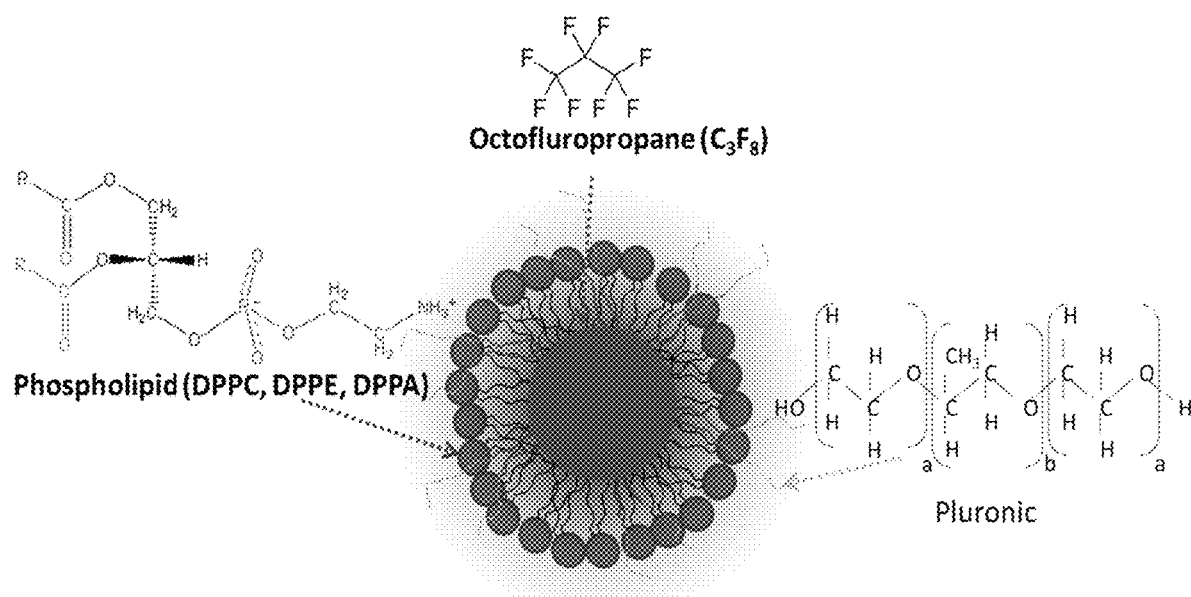
FIG. 5 is a schematic illustration of a nanobubble that is constituted with $C_3F_8$ gas encapsulated with DPPC, DPPE and DPPA lipids and Pluronic shell

Bubbles were prepared by first dissolving DPPC, DPPA and DPPE in chloroform, followed by evaporation of the solvent and hydration with 1×PBS in the presence of glycerol to produce lipid vesicles (FIG. 5). To formulate Pluronic bubbles, Pluronic (Table 2) was either co-dissolved in the chloroform lipid solution before solvent evaporation (prefilm) or was added to the hydration PBS/glycerol solution (postfilm). Hydration of the lipid films took place at 37° C. in an incubator-shaker at 120 RPM for 60 minutes (New Brunswick Scientific). Next, the vials were sealed, the air was withdrawn by a syringe and octafluoropropane was added to the vials until the pressure in the vial was equalized. Finally, the vial was placed on a VialMix™ shaker (Bristol-Myers Squibb Medical Imaging, Inc. N. Billerica, Mass.) for 45 seconds to form the bubbles. Samples were placed on ice immediately after formulation and stored for analysis.

TABLE 2

Experimental Information

| | [Pluronic]; mg/mL | | | |
|---|---|---|---|---|
| | 0.006 | 0.06 | 0.6 | 6 |
| | | Pluronic Mass % | | |
| | 0.075 | 0.75 | 7.5 | 75 |
| | | Lipid/Pluronic Molar Ratio | | |
| L31 | 2051.9 | 205.2 | 20.5 | — |
| L61 | 3730.8 | 373.1 | 37.3 | — |
| L81 | 5409.7 | 541.0 | 54.1 | — |
| L64 | 5129.9 | 513.0 | 51.3 | — |
| P85 | — | 858.1 | 85.8 | 8.6 |

Bubble Sizing and Stability

Bubble size was measured by dynamic light scattering using photon correlation spectroscopy (PCS) at 25° C. (90Plus Brookhaven Instruments Corp). The analysis was done with a laser wavelength of 660 nm at an angle of 90°. Bubble stability in solution over 1 hour was analyzed with dynamic light scattering (DLS) to examine the potential of the bubbles to coalesce. Briefly, 10 µL of bubble stock solution was dissolved in 3 mL of 1 mM KCl in a cuvette at room temperature. Bubble size was determined as above at 0, 15, 30, 45, 60 minutes. The shift in size distribution and polydispersity was noted. These experiments were repeated in triplicate. All bubble sizes presented are based on the number average calculations.

Concurrently, bubbles were exposed to 1X PBS that was pre-heated to 37° C. in a water bath for 0 to 60 minutes. At pre-determined time points, bubble samples were transferred to a hemacytometer and three images (400X) at random fields at each time point per sample were acquired (microscope: Zeiss Axioskop, W.E.L. Instrument CO. LLC; Camera: Zeiss Axiocam MRc5). The number of visible bubbles per image was counted by a custom Matlab program. This program isolated the center of the bubbles and excluded objects based on the size and eccentricity of the object counted. These experiments were also carried out in triplicate. It is important to note that because the smaller-sized bubbles were beyond the resolution of our imaging system; this experiment provides information on stability of the relatively larger bubble (0.4-8 µm) populations.

Zeta Potential Measurements

Zeta potential of each sample was measured using a Zeta Plus Analyzer (Brookhaven Instruments Corp.) by Laser Doppler Anemometry (LDA) using electrophoretic light scattering at 25° C. Test samples for these studies were prepared identically as those for DLS sizing measurements. Dilute particle concentration was maintained to ensure that multiple scattering and particle-particle interactions were negligible. Each sample was run using five repetitions and the average was taken as the final zeta potential.

Bubble Echogenicity In Vitro

In order to characterize the inherent bubble echogenicity with minimal external disturbance, grayscale intensity changes generated by the bubbles were measured in vitro using a linear transducer (Toshiba, Tochigi-Ken, Japan) and a clinical ultrasound scanner (Toshiba Aplio) at 14-MHz (gain: 88; Mechanical Index: <0.1). To carry out the measurements, 400 µL of bubble solution either at the same dilution of stock solution (1:1000) or at the same concentration (3.6E5 bubbles/mL) approximated from the initial hemacytometer data were injected into a custom-designed agarose mold (1% agarose, 99% $H_2O$). Five images of each sample were acquired. The grayscale image intensity was measured with a custom Matlab program, which calculated the mean grayscale value of all nonzero elements in a selected region of interest. This data was normalized to the control. Furthermore, in order to approximate the signal generated by each bubble in the samples of equal dilution (since the absolute number of nanobubbles was considerably greater than that of microbubbles) the signal intensity of each bubble was determined based on the hemacytometer counts and normalized to that of control bubbles.

In addition, since the light microscopy technique has a limited spatial resolution (typically visualizing bubbles >200 nm in diameter), the change in grayscale signal intensity of bubble solution over time was examined to gain further insight regarding stability of the overall bubble population. Samples were diluted (1:1000) in PBS. At t=0, 10, 20 and 30 minutes, 400 µL of sample was transferred to the agarose mold and, as above, five images of each bubble sample were acquired. Here, the grayscale signal intensity of a manually selected region of interest was measured using ImageJ. Measurements at each time point were normalized to the initial values of each sample.

In Vivo Assessment of Nanobubble Contrast

Ten week old female rats (Charles River, Wilmington, Mass.) carrying subcutaneous tumors with size range of 13.16 mm-15.87 mm were used in this study. The tumors were inoculated by injection of 1.0E5 DHD/K12/TRb rat colorectal adenocarcinoma cells originating from chemically-induced adenocarcinoma in the same strain. From the in vitro characterization studies above, the smallest bubbles (those made with Pluronic L61) were selected for the following experiments. To examine nanobubble contrast dynamics in vivo, Pluronic L61 nanobubbles (hydrostatic diameter range: 103-279 nm) and control microbubbles (hydrostatic diameter range: 0.94-1.03 µm) were administered to tumor bearing rats (anesthetized with isoflurane) via bolus injection of 50 µL of bubbles followed by 0.8 mL flush with normal saline into the tail vein. To acquire images, the US probe was immobilized using a clamp and a gel pad was placed between the probe and tumor. After the identification of the tumor with 2D Doppler, harmonic perfusion imaging was used to image changes in the tissue contrast density with time. Images were acquired with a 6 MHz linear transducer (PLT604AT; gain: 90; Mechanical Index: 0.1). Initial image acquisition was started 10 seconds before bubble administration and completed after 60 seconds. Subsequently, 10 second video clips were acquired at t=5, 10, 15 and 20 minutes. Each tumor (8 tumors in 8 animals) received both control bubbles and Pluronic nanobubbles separately in a random order 40 minutes apart.

Image analysis was performed by registering the image series at each time point to the t=0 images using 2D rigid body registration. The transformation optimization was performed with Matlab, using the Nedler-mean simplex algorithm function based on gray-scale similarity, to minimize the sum of the squared difference between pre-bubble injection and post-injection images. Goodness of fit was evaluated by comparing the distance between image edges using a mosaic overlay. The ROI was then selected, and the mean gray-scale value of the ROI was calculated. After the mean gray-scale value was calculated for all time points, the images were normalized by the pre-injection (baseline) value for each animal and the normalized baseline value was subtracted from each time point to give the fold enhancement. To assure proper registration, the t=0 images were registered to themselves.

To further examine contrast dynamics, an additional study was performed using contrast enhanced microflow imaging (MFI). By combining a flash-replenishment (FR) sequence and max-hold processing, MFI has been demonstrated as an excellent tool for revealing the vascular network of lesions. In this imaging procedure, the FR sequence destroys all bubbles in the imaging plane using a burst scan at high MI (set by the manufacturer). Subsequently, during the bubble replenish phase, the maximum bubble intensity at each location is collected and stored until a higher intensity signal at the same location is reached. Then, this higher signal intensity is registered and replaces the previous value using max-hold processing. In this study, using MFI, movies were acquired immediately after bubble injection for 30 seconds (MI: 0.1; frame rate: 15 frames/sec; auto replenish rate: every 10 sec; dynamic range: 90 dB; acoustic frame rate: 45 frames/sec). The max-hold processing was realized at low-mechanical-index (MI: 0.1). MFI data were recorded as AVI clips, and ImageJ was used to extract each video frame. From each video, the first complete 10 seconds of the time intensity (TI) data were extracted and compared.

In Vivo Assessment of Pluronic Nanobubble Efficacy for Enhancing RF Ablation of Rat Tumor This study was designed to determine whether Pluronic delivered by lipid nanobubbles is more effective in enhancing RF ablation of subcutaneous rat tumors compared to free Pluronic. Approximately 6 weeks after tumor inoculation, rats were randomly assigned to 3 groups—RF ablation only, RF ablation+L61 systemic (free Pluronic at 0.3 mg/kg) and RF ablation+L61bubble (L61, 0.3 mg/kg, in the form of nanobubbles). Both L61bubbles and free L61 were administered to the rats via tail vein in bolus 4 hrs (a time chosen based on preliminary unpublished results) before RF ablation using a monopolar RF electrode (21 Gauge custom modified. Tumors were ablated with a typical power of 2-5 watts to achieve an electrode temperature of 80° C. for 3 minutes. Rat weights and tumor sizes measured by calipers were recorded weekly for 4 weeks. Measurement of tumor volume progression was used to assess treatment efficacy.

Statistical Analysis

Two-tailed, unpaired Student's t-test was performed for comparisons of all treatment groups. For multiple comparisons, significance levels were corrected using a Bonferroni adjustment. Unless otherwise noted, all data are reported as mean±SEM (standard error of mean). A P value ≤0.05 was considered statistically significant before Bonferroni correction.

Results

Bubble Size

| | [Pluronic] mg/mL | Diameter (nm) Prefilm; Postfilm | Polydispersity Prefilm; Postfilm | Zeta (mV) Prefilm; Postfilm |
|---|---|---|---|---|
| Control | 0 | 880.9 ± 127.6 | 0.099 ± 0.032 | −55.6 ± 4.2 |
| L31 | 0.006 | 1033.2 ± 133.7; 835.7 ± 75.1 | 0.005 ± 0; 0.005 ± 0 | −46.0 ± 6.5; −48.5 ± 5.1 |
| | 0.06 | 917.9 ± 149.4; 812.3 ± 125.1 | 0.005 ± 0; 0.104 ± 0.055 | −55.6 ± 6.5; −54.1 ± 11.8 |
| | 0.6 | 733.5 ± 159.4; 915.3 ± 77.4 | 0.296 ± 0.010; 0.133 ± 0.036 | −54.4 ± 1.2; −52.0 ± 6.2 |
| L61 | 0.006 | 609.8 ± 24.2; 959.3 ± 194.4 | 0.005 ± 0; 0.107 ± 0.084 | −55.8 ± 12.5; −50.3 ± 1.1 |
| | 0.06 | †526.4 ± 20.9; 641.8 ± 53.0 | 0.124 ± 0.075; 0.162 ± 0.058 | −64.0 ± 5.7; −47.6 ± 3.1 |
| | 0.6 | 371.6 ± 156.3; †207.9 ± 74.7 | 0.225 ± 0.044; 0.227 ± 0.055 | −64.7 ± 4.4; −44.3 ± 2.7 |

-continued

| | [Pluronic] mg/mL | Diameter (nm) Prefilm; Postfilm | Polydispersity Prefilm; Postfilm | Zeta (mV) Prefilm; Postfilm |
|---|---|---|---|---|
| L81 | 0.006 | 882.1 ± 90.0; 782.1 ± 47.9 | 0.005 ± 0; 0.053 ± 0.048 | −41.6 ± 2.6; −40.9 ± 4.5 |
| | 0.06 | 0.06 946.8 ± 151.8; 611.3 ± 90.0 | 0.207 ± 0.054; 0.236 ± 0.032 | −37.4 ± 3.4; −42.3 ± 1.1 |
| | 0.6 | †406.8±21.0; †407.2 ± 84.3 | 0.144 ± 0.073; 0.117 ± 0.073 | −39.4 ± 1.0; −40.3 ± 2.0 |
| L64 | 0.006 | 920.8 ± 58.2; 774.5 ± 100.2 | 0.005 ± 0; 0.005 ± 0 | −41.6 ± 2.6; −56.6 ± 2.6 |
| | 0.06 | 769.0 ± 36.3; 726.3 ± 42.6 | 0.093 ± 0.047; 0.082 ± 0.077 | −46.9 ± 0.9; −44.4 ± 1.6 |
| | 0.6 | 674.6 ± 61.2; 561.0 ± 111.9 | 0.224 ± 0.019; 0.242 ± 0.025 | −39.9 ± 6.3; −36.7 ± 5.9 |
| P85 | 0.006 | ‡1241.0 ± 99.6; 711.8 ± 45.1 | 0.095 ± 0.048; 0.138 ± 0.055 | −54.9 ± 10.0; −49.4 ± 1.7 |
| | 0.06 | 874.6 ± 256.8; 573.2 ± 67.6 | 0.292 ± 0.042; 0.206 ± 0.061 | −66.4 ± 6.2; −53.3 ± 7.6 |
| | 0.6 | 1015 ± 335.3; 570.9 ± 105.8 | 0.200 ± 0.039; 0.295 ± 0.016 | −60.6 ± 7.7; −45.8 ± 6.0 |

†significant difference vs. control
‡significant difference vs. postfilm

Five Pluronics at four different concentrations were tested for their ability to control lipid bubble size (FIG. 6). All Pluronic bubbles were relatively monodispersed with a polydispersity index ranging from 0.005 to 0.296 (Table 3) and all but one (prefilm 0.06 mg/mL P85) had smaller or comparable sizes relative to control bubbles. Smallest bubbles were those made with Pluronic L61 (0.6 mg/mL postfilm 207.9±74.7 nm, P=0.001 compared to control bubbles; and prefilm 371.6±156.3 nm, P=0.05 compared to control bubbles;) followed by L81 (0.6 mg/mL postfilm 407.2±84.3 nm, P=0.01 compared to control bubbles; and prefilm 406.8±21.0 nm, P=0.006 compared to control bubbles). P85 bubbles were larger than control bubbles with prefilm P85 bubbles significantly larger than control bubbles (0.06 mg/mL prefilm: 1241.0±99.6 nm; P=0.05).

Bubble Size Distribution Change as a Function of Time

Bubble size distribution change as a function of time. Data presented for control bubbles and bubbles with 0.6 mg/mL of Pluronic (mean±SEM; n=3). A: prefilm; B: post-film Bubble size was monitored up to 60 min to examine the tendency of the bubbles to coalesce and form larger bubbles. With the exception of P85 bubbles, bubble size remained relatively constant and showed no significant increase within the 60 min analysis period (FIG. 7). For clarity, data is shown only for bubbles with 0.6 mg/mL Pluronic. Bubbles made with the post-film addition of Pluronic appeared to show less size variation over the time period and bubbles with L61 and L81 showed the most consistent stability. All bubbles in the presence of P85 showed a time dependent size growth.

Bubble Rate of Dissolution

The relative change in bubble stability was monitored for 60 min at 37° C. in vitro. Here, stability was defined as the robustness or rate of dissolution of bubbles in solution. Data were normalized based on the initial bubble concentrations at t=0. Again, for clarity, representative data of control bubbles and bubbles at 0.6 mg/mL of Pluronic are presented (FIG. 8). In general postfilm bubbles appeared to have better stability compared to prefilm bubbles, but in both groups, bubble loss was evident after 15 minutes. All bubble concentrations (P: 0.0001-0.023) decreased significantly at t=60 min compared to that at t=0, except prefilm L31 bubbles (P=0.1). After 60 min, control bubbles decreased to 60.8±8.4% (P<0.001) of their initial concentration compared to 19.2 to 74.8% for prefilm Pluronic bubbles, and 20.4 to 84.4% for postfilm Pluronic bubbles. Again, it is important to note that because these stability measurements were carried out using microscopy, it is possible that smaller bubbles were omitted in the final analysis. This may account for the apparently lower stability of the nano-sized vehicles.

Zeta Potential

Zeta potential measurement provides information on the stability of particle in suspension and is a function of particle surface charge (Table 3). Our results showed that control bubbles had net negative charge of −55.6±4.2 mV. These bubbles are stable and have a negatively-charged surface due to the presence of DPPA. In the presence of Pluronic, no significant difference in bubble surface charge was detected; the zeta potentials ranged between −64.7±4.4 mV to −37.4±3.4 mV for prefilm Pluronic, and between −50.3±1.1 mV to −40.3±2.0 mV for postfilm Pluronic bubbles.

The grayscale ultrasound signal intensity was quantified to determine the change in signal for each bubble formulation. Ultrasound images were acquired in custom designed agarose molds (FIG. 9A-B). Images of bubbles at 0.6 mg/mL of Pluronic under the same dilution (1:1000; FIG. 9C) are shown. For comparison of echogenicity per bubble, (FIG. 9D) shows images of bubbles that were diluted to the same concentration (3.6E5 bubbles/mL) using the initial hemacytometer counts reported above. Results confirmed that all Pluronic bubbles yield ultrasound signals comparable to larger control bubbles (FIG. 10). None of the Pluronic bubbles showed significantly lower ultrasound signal intensity compared to control bubbles. In addition, bubbles with both low (prefilm: 345.3±28.0%; postfilm: 53.5±12.3%) and high concentrations of postfilm P85 had significantly higher grayscale signal intensity than control bubbles ($P<0.008$).

Grayscale Signal Intensity Changes Over Time

FIG. 9A shows the experimental set up of the study (dashed lines indicate the sample well). A representative image of the sample medium, $H_2O$, is shown in FIG. 9B. Results showed that the initial grayscale signal intensity of control microbubbles was 79.1±3.0 and that of L61 nanobubbles was 74.8±16.3 (Mean±SEM; n=3). Most importantly, at 30 minutes, the signal intensity of control microbubbles decreased significantly (53.3±4.7%) compared to t=0 (P=0.0006) while no significant decrease in the signal intensity of L61 nanobubbles was observed (70.3±9.4%; FIG. 11).

Nanobubble-Enhanced In Vivo Tumor Perfusion Imaging

All tested bubbles were visible in vivo (FIG. 12). Data from 2/8 animals were excluded from the final analysis because of excessive signal noise. Initial tumor enhancement with L61 nanobubbles showed a 50% increase over control bubbles (n=6). Five minutes post injection, the enhancement with nanobubbles was 30% less than control. At subsequent time points (10, 15 and 20 min), the enhancement was t=0 t=10 min t=20 min t=30 min consistently greater with the nanobubbles compared to microbubbles, however the differences were not statistically significant.

Nanobubble-Enhanced In Vivo Tumor Microflow Imaging

Microflow imaging (MH) was carried out on eight rats. One animal died immediately after control bubble injection and was excluded from the study. FIG. 13A shows a representative set of MFI images of a tumor following injection of L61 nanobubbles (FIG. 13B) and control microbubbles (FIG. 13C). Overall 6/7 tumors showed considerably improved enhancement when imaged with L61 nanobubbles compared to control microbubbles. Contrast enhancement with nanobubbles also reached maximum intensity faster than control microbubbles.

Figure 14:
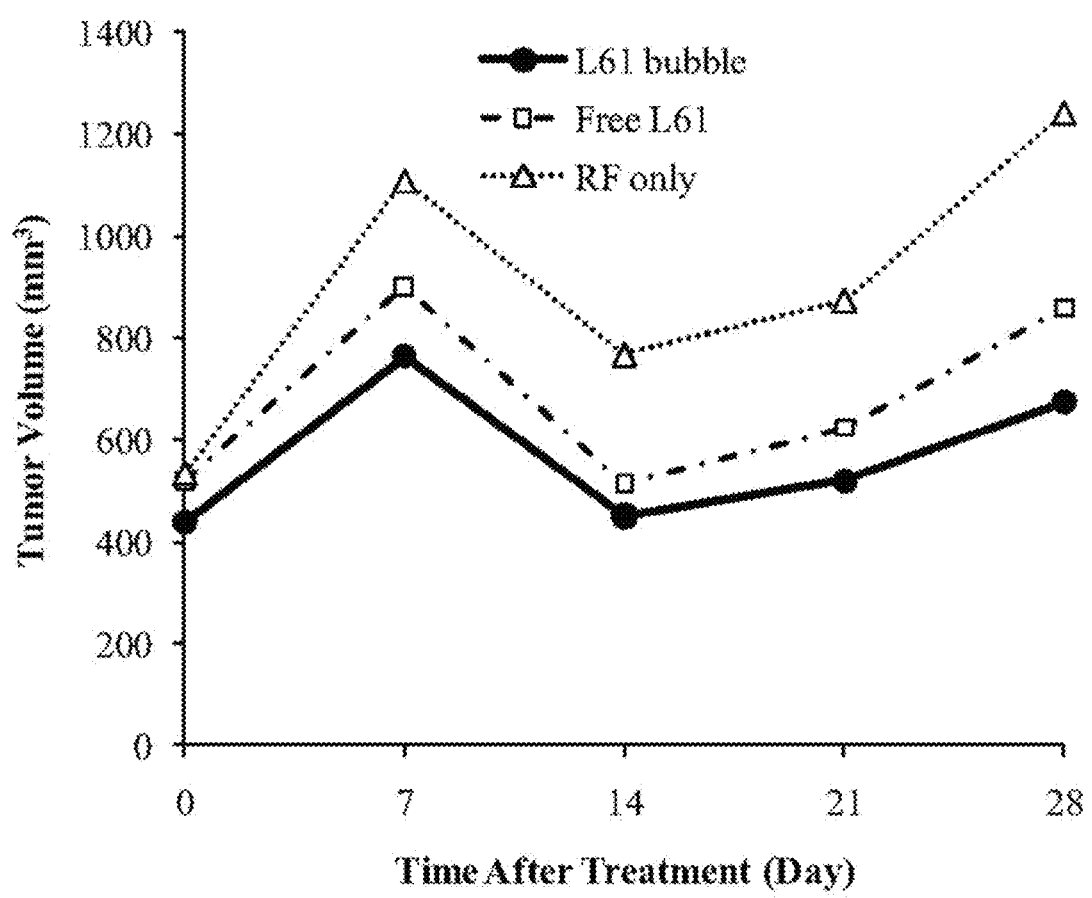
FIG. 14 is a plot illustrating tumor volume changes after RF ablation in the presence or absence of Pluronic L61 delivered as free agents or via lipid nanobubbles (n=14 or 16).

In Vivo Assessment of Pluronic Nanobubble Efficacy for Enhancing RF Ablation of Rat Tumor Our results (FIG. 14) showed that at 7 days, among all treatment groups, tumors treated with L61 nanobubble+RF ablation showed the least tumor volume increase compared to the pretreatment volumes followed by those of tumors receiving free L61+RF ablation and RF ablation only. This observation may indicate that Pluronic L61 reduces the inflammatory response of the tissue after RF ablation which is consistent with our previous published data showing that Pluronic P85 was also able to reduce the inflammatory response of the tissue. In addition, tumor volumes from the L61 nanobubble+RF ablation treatment group were smaller than those treated with free L61+RF ablation over the entire treatment time. This may indicate that more Pluronic has been delivered to the tumor site using L61 nanobubbles (Pluronic pharmacokinetic studies are undergoing). However, there is no statistically significant improvement in treatment outcome when comparing shrinkage of those tumors treated with L61 delivered in the bubble vs. free L61. This may be explained by the treatment protocol which caused severe under ablation of the tissue, leading to imperceptible tumor size changes. While there are questions on the design of the treatment protocol, it is not an unreasonable expectation that if the ablation power were higher, there could be much more pronounced effects when using the nanobubble delivery system. This work also provides a basis for the use of low frequency ultrasound as external stimuli to break the bubbles and release the Pluronic at the site of action. With the external stimuli, a higher Pluronic accumulation at the tumor site and the prevention of any potential high Pluronic dose related toxicity is anticipated.

The results demonstrate that while all tested Pluronic play a role in modulation of bubble size, Pluronic L61 and L81 at a loading of 0.6 mg/mL were most effective in reducing it. L61 and L81 bubbles were closer to a desirable 100-300 nm range. Compared to the larger control bubbles, these nanobubbles may be more advantageous for cancer targeting in two ways. First, the small size and hydrophilic PEO segments of Pluronic, which helps transform the bubbles into a structure similar to the stealth liposome, will likely prolong their blood pool circulation time since the larger bubbles (>1 μm) are more prone to clearance by the reticuloendothelial system (RES) after intravenous injection. Second, also attributable to the small size, these nanobubbles are more likely to reach the smallest capillaries and may be able to extravasate the leaky vasculature of tumor with more ease than the micrometer control bubbles. These theories may help explain why tumor volume increases are less drastic when treated with L61 nanobubbles compared to those treated with free L61 before RF ablation. These properties are also likely to make nanobubbles superior candidates for drug delivery or for applications in contrast enhanced tumor imagining that could take advantage of the EPR effect. Unlike L61 and L81, the relatively high Mw Pluronic P85 at 0.06 mg/mL resulted in bubbles that were significantly larger than control ones. The distinctive behavior between P85 and L61 or L81 may be explained by two intrinsic properties of the Pluronic molecules: the Mw and hydrophiliclipophilic balance (HLB) or relative hydrophobicity. At lower Pluronic concentrations, there is a higher lipid to Pluronic molar ratio (Table 2), and the presence of Pluronic is relatively insignificant to the overall free energy of the system, thus Pluronic has minor effects on bubble size control, providing that the Pluronic has a relatively low Mw, as is the case for Pluronic L61 and L81. Unlike L61 and L81 which fit between the lipid molecules in a manner similar to cholesterol and improve the packing of the lipids in the bubbles, P85 is larger, bulkier and more hydrophilic; although it is able to incorporate between the lipid molecules, the long hydrophilic ethylene oxide groups protrude outside of the lipid shell increasing the overall size of the bubbles. At higher concentrations, there is a much lower lipid to Pluronic molar ratio (Table 2), and the free energy of the bubble system is disturbed by the presence of Pluronic molecules. At a threshold molar ratio, some transformation becomes necessary to increase the entropy of the system to accommodate the free energy change. P85, a bulky and hydrophilic molecule, has a weaker membrane penetration ability, and the necessary transformation the system has to undergo is squeezing out P85 molecules of the lipid shell to increase the entropy. Hence, at higher concentrations, P85 loses its ability to control bubble size, which is in agreement with our results. In contrast, L61 and L81 are very hydrophobic and have higher membrane penetration ability, and hence are not easily squeezed out of the membrane. To accommodate that, a size decrease of the bubbles may become a necessary means for the system to stay in equilibrium.

Our results also showed that bubble size is inversely related to Pluronic concentration. FIG. 15 demonstrates the inverse relationships between Pluronic concentration and bubble size for L81 and L61 bubbles (R2 values of 0.96 (prefilm) and 0.86 (postfilm) for L81 and 0.93 (prefilm) and 0.88 (postfilm) for L61). The high negative zeta potential values of these bubbles further refute the potential for coalescing with each other. The decrease in bubble concentration but relatively constant (or in the case of L61 and L81 decreasing) size distribution may be explained by the experimental technique used to obtain bubble counts, which had limited resolution and was unable to image majority of the nanobubbles. Thus, bubble concentration change provides information on stability of relatively large bubbles. However, overall, the bubbles, particularly those made with post-film addition of Pluronic appear to have comparable stability to that of control bubbles. While the small radius of the nanobubbles is not favorable for its stability according to the following relationship: $T=\rho R^2/2DC_3T$: microbubble persistence in the aqueous solution, p: gas density, R: initial radius of the bubble and D: diffusion coefficient of the gas; the loss of bubble stability due to the reduction of size may be compensated by the Pluronic surfactant induced decrease in bubble surface tension, which is also a factor affecting bubble stability.

While small UCA may be essential for drug and gene delivery, and contrast enhanced imaging, the tradeoff of their signal intensity has been a constant concern. Both in vitro and in vivo, ultrasound imaging studies have demonstrated that the echogenicity of our nanobubble system was not compromised compared to the control microbubbles. This may be explained by 1) a greater absolute number of nanobubbles compared to the larger control bubbles, and 2) the Pluronic induced membrane fluidity increase which balances the loss of acoustic signal caused by bubble size reduction according to the acoustic theory. Studies have shown that Pluronic is able to increase the cell membrane fluidity. Although consistent trends indicating improved tumor enhancement over 20 minutes were seen with nanobubbles versus microbubbles, no significant differences were noted.

We have thus demonstrated that Pluronic triblock copolymers can be used for simple formulation of relatively stable echogenic lipid nanobubble UCA. Our results have shown that 1) Pluronic is effective in reducing bubble size, 2) the size control is dependent on Pluronic Mw, hydrophobicity and PO block length; and 3) once the appropriate Pluronic structural requirements are met, the bubble size decreased with an increase in Pluronic concentration. Furthermore, 4) the bubble stability and echogenicity do not appear to be compromised due to bubble size reduction. Most importantly, 5) our results demonstrated that it is more efficacious to use L61 nanobubbles than free L61 for enhancing RF ablation.

Example 2

In the previous Example, we demonstrated that Pluronics were effective in sensitizing cancer cells to low grade hyperthermia and reducing lipid shelled bubble size. In this Example, we aimed to identify the specific Pluronic structural properties that are critical to its cancer cell thermosensitizing ability (function 1) and its modulation of lipid bubble size (function 2). The initial results showed that both of these Pluronic functions are molecular weight (Mw) dependent through 2nd order polynomials. For thermosensitizing ability, two groups of Pluronic have demonstrated satisfactory potency under tested conditions. First group are those polymers with Mw≤2500 Da, HLB between 1-7 and having polypropylene chain length that are even multiples of the length of fatty acids tails (16 carbons) of the membrane phospholipids. The second group also comprised Pluronic with polyethylene chain length that are even multiples of the length of fatty acids that with 16 carbons, but with Mw≥2750 Da and HLB>7. For the ability to reduce bubble size, our results showed that Pluronic Mw is the major contributor, and Pluronic with Mw around 2200 Da are the ideal candidates. To validate the structure function relationships, additional polymers were selected based on predictions generated from the fitted curves, and their ability to sensitize cancer cells to hyperthermia and to modulate bubble size were examined. Results demonstrated that these new data obeyed the initial predictions and confirmed that Pluronic structure is essential to its function. Due to the duality of the role Pluronic plays in this work, the best candidate will be the one that shows the most potent thermosensitizing ability to cancer and is able to reduce lipid bubble size below 250 nm in diameter. Our results indicate that L61 is the polymer of choice.

In this Example, the thermosensitizing effects of L61 in vivo and the effect of additional Pluronic other than L61 and P85 in vitro is discussed. Then, the specific Pluronic structural properties that are critical for their ability to thermosensitize cancer cells and modulate lipid bubble size will be discussed.

In Example 1, we designed, formulated and characterized lipid shell stabilized nanobubbles using Pluronic as the size modulator. Bubbles were formulated with the presence of several type of Pluronic with varying concentration, Mw and hydrophobicity. Our results showed that multiple types of Pluronic (L61 and L81) were able to reduce the lipid bubble size below 250 nm. We speculated that Pluronic structural properties are the contributing factors for their ability to modulate bubble size. In this section, we aimed to devise some simple models that will predict the best Pluronic candidates which would provide optimal bubble size modulation.

Bubble formulation and characterization are described in Example 1. All curves are fitted with Microsoft Excel. Unless otherwise noted, data are presented as mean±SEM (standard error of mean).

Results and Discussion

Figure 16:
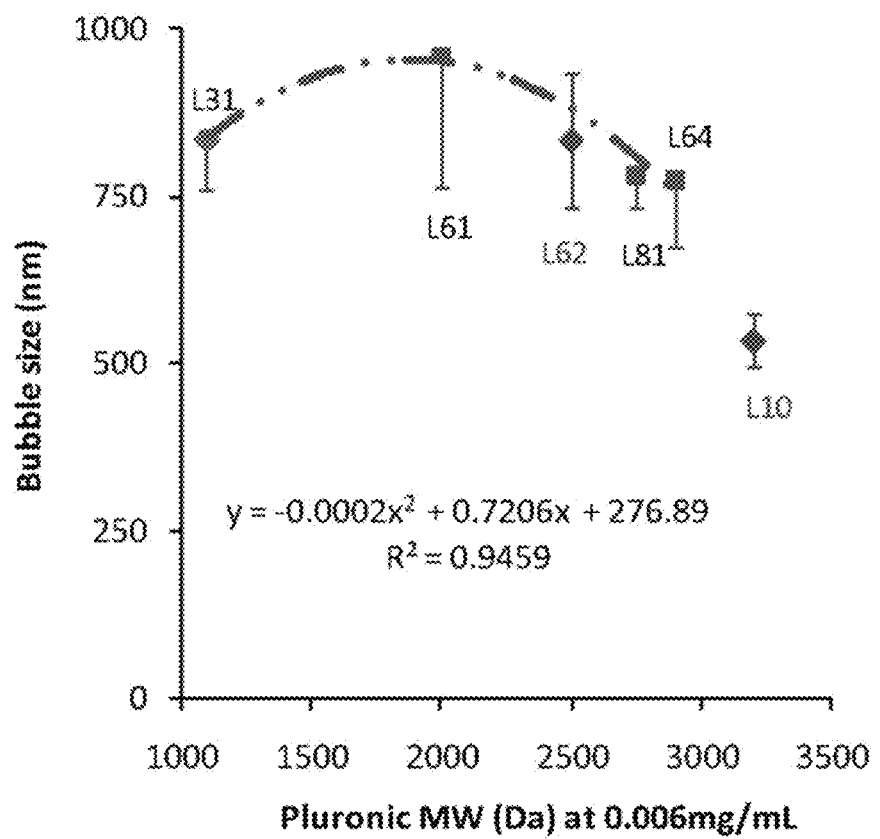
FIG. 16 is a plot illustrating a relationship between bubbles size and Pluronic Mw at 0.006 mg/mL of Pluronic. Error bars are Mean±SEM (standard error of mean).
Figure 17:
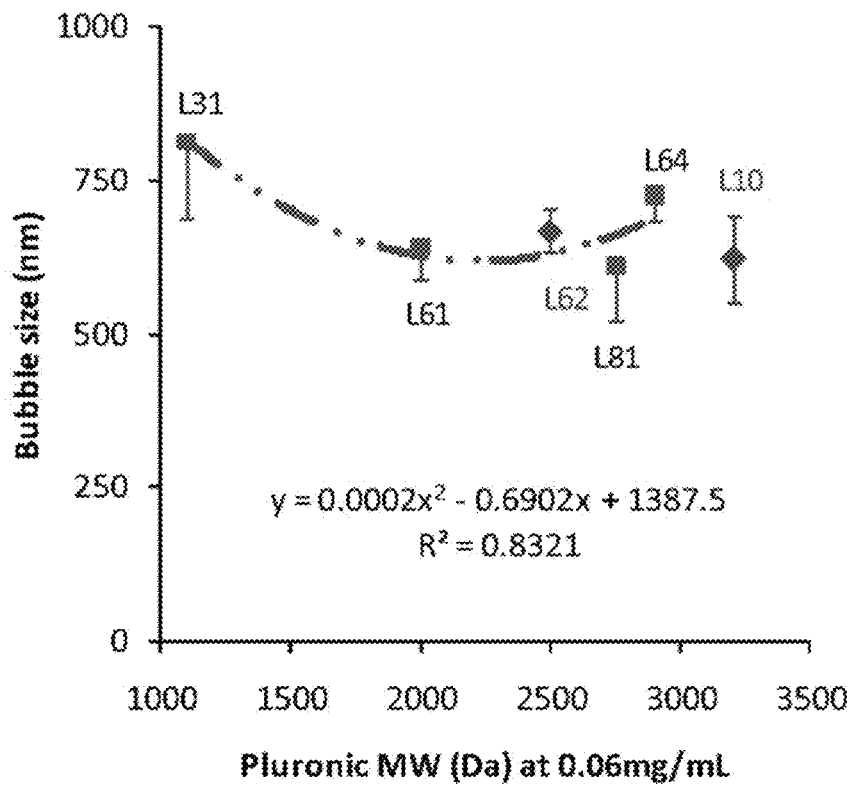
FIG. 17 is a plot illustrating a relationship between bubbles size and Pluronic Mw at 0.06 mg/mL of Pluronic. Error bars are Mean±SEM (standard error of mean).
Figure 18:
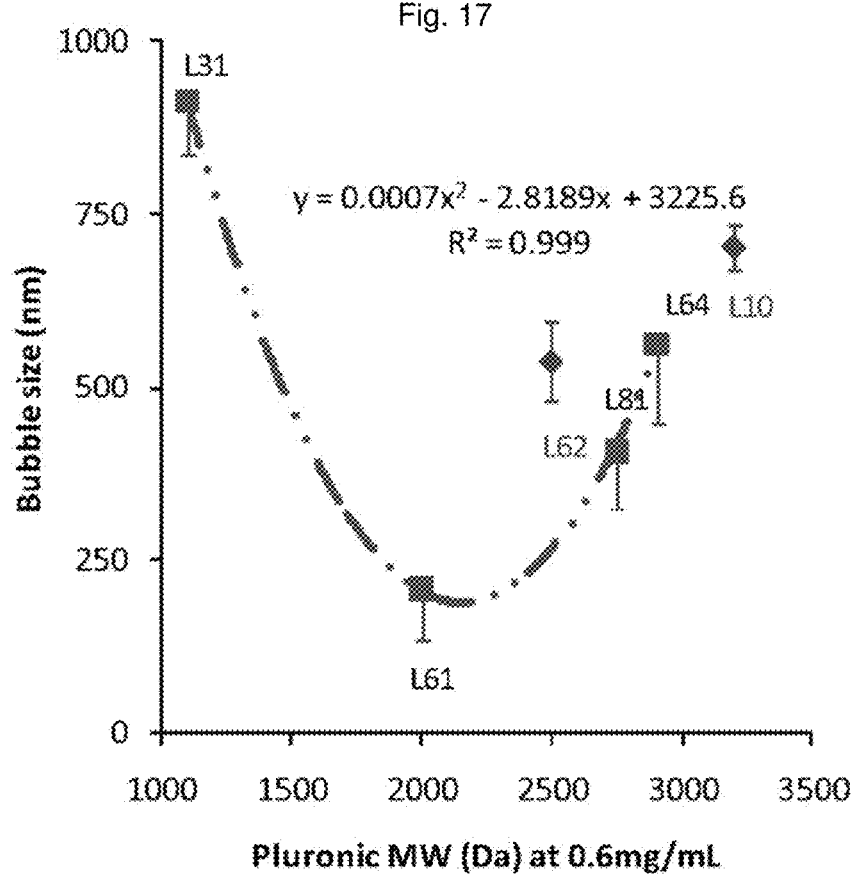
FIG. 18 is a plot illustrating a relationship between bubbles sizes and Pluronic Mw at 0.6 mg/mL of Pluronic. Error bars are Mean±SEM (standard error of mean).

Bubble sizes (number average diameter) were correlated to various parameters including Npo/Nep ratio, Mw, HLB and Npo. Our data showed that the most apparent correlations are the ones between the bubble sizes and the molecular weights of Pluronic which were fitted by $2^{nd}$ order polynomials. FIGS. 16-18 show the fitted functions at three different Pluronic concentrations (0.006, 0.06 and 0.6 mg/mL). At all Pluronic concentrations, the bubble sizes followed $2^{nd}$ order, $y=ax^2+bx+c$, polynomial functions against molecular weights with $R^2$ value of 0.9459 and a=−0.0002 showing an excellent fit at 0.006 mg/mL, the lowest Pluronic concentration tested. The R2 values and the coefficient of the $2^{nd}$ order term are 0.8321 and 0.0002 at 0.06 mg/mL Pluronic, and they are 0.999 and 0.0007 at 0.6 mg/mL of Pluronic sequentially. Interestingly, with increase of Pluronic concentration, while the relationships between bubbles sizes and Pluronic molecular weights remained 2nd order polynomials, the characteristic of the curves have changed. The coefficients of the 2nd order term become more positive with increasing Pluronic concentrations. At 0.06 mg/mL of Pluronic, this coefficient is 0.0002; and at 0.6 mg/mL, it is 0.0007. In addition, the absolute value of "a", the coefficient of the 2nd order term, increases leading to a narrower upward parabola at higher Pluronic concentration (FIG. 18).

The characteristics of these functions reveal that the bubble sizes becomes less dependent on Pluronic concentrations at either the lower end (<1100 Dalton) or the higher end (>3000 Dalton) of the Pluronic molecular weight spectrum, however, the bubble sizes do depend on the Pluronic concentration at the intermediate Pluronic molecular weights (1100<Mw<3000 Dalton) with the bubbles sizes becoming smaller at increasing Pluronic concentrations. Finally, these models suggest that at lower concentrations, Pluronic effects on bubbles size are minute.

The ability of Pluronic L10 and L62 to modulate bubble size was also investigated to validate the fitted curves. We choose these Pluronics because of their dual roles in this dissertation work, as a sensitizing agent, which is an active biological modifier, and as the bubble size modulator, an active thermodynamic (mechanical) role. In the previous section, we predicted and confirmed that L10 and L62's act as biological modifiers. Here we want to see whether they also obey the fitted models for their other role as lipid bubbles size modulators. From these results we can deduce that both polymers are in relatively good agreement with the fitted models.

It is unclear how Pluronic reduces the sizes of bubbles. However, one potential means is by changing the curvature of the bubble shells. FIG. 2 illustrates this potential mechanism. The hypothesis is that Pluronic molecules due to their specific geometry cause the increase in the bubble lipid shell curvature. At the same arc length, the higher the bubble shell curvature, the smaller the bubble sizes.

Example 3

Effective tumor-targeted drug delivery systems should be specific, minimally or non-invasive, and controllable. Traditional treatment methods generally lack one or more of those characteristics. This Example describes a system consisting of an in situ forming PLGA implant, lipid nanobubbles, and ultrasound radiation. In situ forming biodegradable polymer implants are injected as a solution of polymer, solvent, and drug, which solidifies in the tumor tissue through phase inversion. The period closely following injection is the burst period of polymer precipitation, which is followed by a more sustained drug release resulting from a combination of polymer degradation and drug diffusion. The controllability of these in situ forming implants could be improved by applying ultrasound irradiation, which has been shown to increase drug release from, and polymer degradation of, biodegradable polymer implants. Ultrasound-induced cavitation of biotinylated nanobubbles bonded to an avidin-conjugated implant could potentially further stimulate controlled release by microscopically damaging the implant surface and causing more drug diffusion. The cavitation effects would also increase cell and tissue permeability, allowing enhanced cell uptake of the drug at the site of sonication. This Example demonstrates that the proposed minimally invasive drug delivery system creates a drug depot with the potential for on-demand drug delivery directly to the tumor.

Materials & Methods

Nanobubbles: A lipid mixture consisting of 1,2-dipalmitoyl-sn-glycero-3-phosphocholine (DPPC), 1,2-dipalmitoyl-sn-glycero-3-phosphoethanolamine (DPPE), and 1,2-dipalmitoyl-sn-glycero-3-phosphate (DPPA) was dissolved in chloroform. Biotinylated bubbles included DPPE-PEG-Biotin. The solvent was evaporated from the solution to create a homogeneous lipid film, which was then incubated with glycerol and phosphate-buffered saline (PBS). Octafluoropropane gas (C3F8) was inducted into the sealed vial, and the vial contents were mechanically shaken.

Implants: Polymer solutions were comprised of 1-methyl-2-NMP), 50:50 poly(D,L-lactide-co-glycolide) (PLGA) (3A), and fluorescein (mock drug) in a 60:39:1 mass ratio. Avidin-conjugated PLGA replaced the PLGA in the avidin-PLGA solutions, which had a 75:24:1 mass ratio (NMP:PLGA:fluorescein).

Ultrasound-Stimulated Drug Release

Implant formation began when the polymer solution was dropped into PBS. The experimental implant mass was recorded. The PLGA implant in PBS was then placed in a shaking incubator.

Four hours after the implant was dropped, it was removed from the PBS and placed in a well with microbubble solution to receive ultrasound radiation at 0.5 W/cm2 with constant stirring. Control implants were placed in diH$_2$O, either with or without sonication. The microbubble and diH$_2$O solutions were sampled after sonication to determine immediate drug release. The implant was put into PBS and returned to the incubator.

The PBS supernatant around the implant was sampled and replaced at 4 hrs (prior to implant sonication), 8 hours, and 30 hours to determine extended drug release.

Fluorescence scans determined the amount of fluorescein in each sample. Samples containing residual microbubbles were centrifuged to minimize microbubble interference in the fluorescence readings.

Avidin-conjugated implants were studied as described above, using the PLGA-avidin polymer solution. These implants were sonicated in a solution of biotinylated nanobubbles at 3 hrs, and PBS supernatant was sampled and replaced at 3 and 9 hrs.

Results

Regular PLGA implants generally released less fluorescein, both during immediate and extended release, than did avidin-conjugated PLGA implants. When compared to implants with the same polymer composition that were exposed to ultrasound alone, regular PLGA implants subjected to ultrasound plus microbubbles had 66% higher fluorescence levels immediately following sonication whereas avidin-conjugated PLGA implants receiving ultrasound with biotinylated nanobubbles had 236% higher fluorescence levels. Both for regular and avidin-conjugated PLGA implants, the combination of nanobubbles and sonication did not appear to greatly alter the extended release profiles of the implants compared to implants receiving no ultrasound nor nanobubbles and implants treated with ultrasound alone. The results suggest a potential for "on-demand" drug release from avidin-conjugated PLGA implants when biotinylated nanobubbles are attached to the implant surface and the system is sonicated.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method for imaging a region of interest (ROI) in a subject, the method comprising the steps of:
administering to the subject a composition comprising a plurality of stabilized nanobubbles, each of the nanobubble having a membrane that defines an internal void, which includes at least one gas, the membrane including a plurality of lipids and poloxamers that are incorporated between lipids of the membrane and that is are effective to control the size of the nanobubble without compromising in vitro and in vivo echogenicity of the nanobubble, each poloxamer having a molecular weight of 1100 Da to 4600 Da, and each nanobubble having a diameter of about 50 nm to about 800 nm and a poloxamer concentration of 0.06 mg/ml to 6 mg/ml; and
generating at least one image of the ROI.

2. The method of claim 1, further comprising the step of generating at least one baseline image of the ROI prior to administering the composition.

3. The method of claim 1, each nanobubble having an average diameter of about 100 nm to about 600 nm.

4. The method of claim 1, at least one poloxamer comprising the chemical formula of:
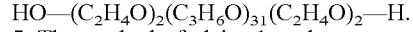

5. The method of claim 1, at least one poloxamer comprising the chemical formula of:
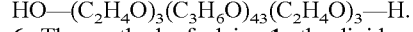

6. The method of claim 1, the lipids comprising 1,2-dipalmitoyl-sn-glycero-3-phosphocholine, dipalmitoyl-sn-glycero-3-phosphoethanolamine, and dipalmitoyl-sn-glycero-3-phosphate.

7. The method of claim 1, each nanobubble having a lipid:poloxamer molar ratio of about 30:1 to about 40:1.

8. The method of claim 1, each nanobubble having a lipid:poloxamer molar ratio of about 40:1 to about 50:1.

9. The method of claim 1, the poloxamers having a hydrophobic/lipophilic balance (HLB) between about 1 to about 7.

10. A method for treating a neoplastic disorder in a subject, the method comprising:
administering to neoplastic cells of the subject a composition comprising a plurality of stabilized nanobubbles, each of the nanobubbles having a membrane that defines an internal void, which includes at least one gas, the membrane including a plurality of lipids and poloxamers that are incorporated between lipids of the membrane and that are effective to control the size of the nanobubbles without compromising in vitro and in vivo echogenicity of the nanobubbles, each poloxamer having a molecular weight of 1100 Da to 4600 Da, and each nanobubble having a diameter of about 50 nm to about 800 nm and a poloxamer concentration of 0.06 mg/ml to 6 mg/ml.

11. The method of claim 10, further comprising applying a cellular stress to the neoplastic cells of the subject at an amount or level effective to induce heat shock protein (HSP) expression in the neoplastic cells and the plurality of nanobubbles being administered to the neoplastic cells at an amount effective to substantially inhibit HSP expression and/or function in the neoplastic cells.

12. The method of claim 11, the cellular stress applied to the neoplastic cells selected from the group consisting of radiotherapy, radiation, and hyperthermia.

13. The method of claim 10, each nanobubble having an average diameter of about 100 nm to about 600 nm.

14. The method of claim 10, at least one poloxamer comprising the chemical formula of:
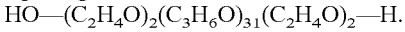

15. The method of claim 10, each nanobubble having a lipid:poloxamer molar ratio of about 30:1 to about 40:1.

16. The method of claim 10, at least one poloxamer comprising the chemical formula of:
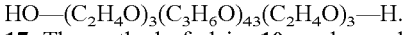

17. The method of claim 10, each nanobubble having a lipid:poloxamer molar ratio of about 40:1 to about 50:1.

18. The method of claim 10, the lipids comprising 1,2-dipalmitoyl-sn-glycero-3-phosphocholine, dipalmitoyl-sn-glycero-3-phosphoethanolamine, and dipalmitoyl-sn-glycero-3-phosphate.

19. The method of claim 10, the nanobubbles further comprising at least one targeting moiety that is linked to the membrane of at least one nanobubble, the targeting moiety promoting targeting and/or adherence of the nanobubbles to the neoplastic cells.

20. The method of claim 10, the targeting moiety being selected from the group consisting of polypeptides, polynucleotides, small molecules, elemental compounds, antibodies, and antibody fragments.

21. The method of claim 10, the composition further comprising at least one chemotherapeutic agent or anti-proliferative agent.

22. The method of claim 21, the at least one chemotherapeutic agent or anti-proliferative agent being contained within the membrane or conjugated to the membrane of the nanobubble.

23. The method of claim 10, the poloxamers having a hydrophobic/lipophilic balance (HLB) between about 1 to about 7.

* * * * *